(12) United States Patent
Asefa et al.

(10) Patent No.: US 9,176,140 B2
(45) Date of Patent: Nov. 3, 2015

(54) CORRUGATED AND NANOPOROUS MICROSTRUCTURES AND NANOSTRUCTURES, AND METHODS FOR SYNTHESIZING THE SAME

(75) Inventors: Tewodros Asefa, Somerset, NJ (US); Yan-Li Shi, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 1190 days.

(21) Appl. No.: 12/566,385

(22) Filed: Sep. 24, 2009

(65) Prior Publication Data
US 2010/0093013 A1  Apr. 15, 2010

Related U.S. Application Data

(60) Provisional application No. 61/099,641, filed on Sep. 24, 2008.

(51) Int. Cl.
*G01N 33/58* (2006.01)
*B81C 99/00* (2010.01)
*G01N 33/543* (2006.01)
*B01J 21/08* (2006.01)

(52) U.S. Cl.
CPC .......... *G01N 33/587* (2013.01); *B81C 99/0095* (2013.01); *G01N 33/54353* (2013.01); *B01J 21/08* (2013.01)

(58) Field of Classification Search
None
See application file for complete search history.

(56) References Cited

U.S. PATENT DOCUMENTS

| | | | | |
|---|---|---|---|---|
| 5,334,296 A * | 8/1994 | Henkens et al. | ........... | 205/777.5 |
| 5,350,484 A * | 9/1994 | Gardner et al. | ............... | 438/669 |
| 5,757,124 A * | 5/1998 | Pope | ............................. | 313/495 |
| 5,789,148 A * | 8/1998 | Van Vlasselaer et al. | ......... | 435/2 |
| 6,584,807 B1 * | 7/2003 | Tregoat et al. | .................. | 65/386 |
| 6,803,019 B1 * | 10/2004 | Bjornson et al. | ................ | 422/66 |
| 7,128,884 B2 * | 10/2006 | Kirkland et al. | ............. | 423/335 |
| 7,303,862 B2 * | 12/2007 | David | .......................... | 430/322 |
| 7,776,611 B2 * | 8/2010 | Crudden et al. | ............. | 436/171 |
| 7,862,892 B2 * | 1/2011 | Chan et al. | .................... | 428/403 |
| 8,075,664 B1 * | 12/2011 | Wang et al. | ..................... | 75/370 |
| 8,216,961 B2 * | 7/2012 | Lee | ............................... | 502/240 |

OTHER PUBLICATIONS

Turkevich, J., Stevenson, P.C, Hillier, J., "A Study of the Nucleation and Growth Processes in the Synthesis of Colloidal Gold",Discuss. Faraday Soc, Jan. 1, 1951, 11, pp. 55-75. DOI: 10.1039/DF9511100055.*

(Continued)

*Primary Examiner* — Rosanne Kosson
*Assistant Examiner* — Aaron J Kosar
(74) *Attorney, Agent, or Firm* — Frederick J. M. Price; George R. McGuire; Bond Schoeneck & King

(57) ABSTRACT

A method of synthesizing corrugated and nanoporous microspheres including the steps of synthesizing substantially smooth spherical microspheres, and controlled wet-etching of the substantially smooth spherical microspheres with a basic solution having a pH above 10.00 is provided. The microspheres can include, for example, silica microspheres or titania microspheres of various sized diameters of between 50 nm and 600 nm. The basic solution can include an aqueous potassium cyanide solution or an aqueous potassium hydroxide solution. Methods of using the corrugated and nanoporous microspheres described herein are also provided.

17 Claims, 18 Drawing Sheets

(56) References Cited

OTHER PUBLICATIONS

Wang, Y., Ibisate, M., Li, Z., Xia, Y., "Metallodielectric Photonic Crystals Assembled from Monodisperse Spherical Colloids of Bismuth and Lead", Advanced Materials, 2006, vol. 18 pp. 471-476. DOI: 10.1002/adma.200502047.*

Kumar, A., Pushparaj, V., Murugesan, S., Viswanathan, G., Nalamasu, R., Linhardt, R., Nalamasu, O., Ajayan, P., "Syntheses of Silica-Gold Nanocomposites and Their Porous Nanoparticles by an In-Situ Approach", Langmuir, 2006, vol. 22, pp. 8631-8634. DOI: 10.1021/la060869g.*

Morinaga, T., Ohkura, M., Ohno, K., Twujii, Y., Fukuda, T., Momodisperse Silica Particles Grafter with Concentrated Oxetane-Carrying Polymer Brushes: Their Synthesis by Surface-Initiated Atom Transfer Radical Polymerization and Use for Fabrication of Hollow Spheres, Macromolecules, 2007, pp. 1159-1164, vol. 40.

Sood, S., Peelamedu, R., Sundaram, K., Dein, E., Todi, R., Wet Etching of Sputtered Tantalum Thin Films in NaOH and KOH Based Solutions, Journal of Material Science, 2007, pp. 535-539, vol. 18.

Cesano, F., Groppo, E., Bonino, F., Damin, Lamberti, C., Bordiga, S., Zecchina, A., Polyethylene Microtubes from Silica-Based Polyethylene Composites Synthesized by Using an in Situ Catalytic Method, Advanced Materials, 2006, pp. 3111-3114, vol. 18.

Gomez, J., Sandoval, J., The Effect of Conditioning of Fused-Silica Capillaries on their Electrophoretic Performance, Electrophoresis, 2008, pp. 381-392, vol. 29.

Chang-Chien, C., Hsu, C., Lin, H., Tang, C., Lin, C., Synthesis of Porous Carbon and Silica Spheres Using PEO-PF Polymer Blends, Journal of Porous Materials, 2006, pp. 195-199, vol. 13.

Bohme, R., Pissadakis, S., Ruthe, D., Zimmer, K., Laser Backside Etching of Fused Silica with Ultra-Short Pulses, Applied Physics A, 2006, pp. 75-78, vol. 85.

Wang, Y., Ibisate, M., Li, Z., Xia, Y., Metallodielectric Photonic Crystals Assembled from Monodisperse SPerical Colloids of Bismuth and Lead, Advanced Materials, 2006, pp. 471-476, vol. 18.

Landon, P., Glosser, R., Self-Assembly of Sperical Colloidal Silica Along the [100] Direction of the FCC Lattice and Geometric Control of Crystallite Formation, Journal of Colloid and Interface Science, 2004, pp. 92-96, vol. 276.

Eidan-Assmann, S., Widoniak, J., Maret, G., Synthesis and Characterization of Porous and Nonporous Monodisperse Colloidal TiO2 Particles, Chemistry of Materials, 2004, pp. 6-11, vol. 16.

Turkevich, J., Stevenson, P., Hillier, J., A Study of the Nucleation and Growth Processes in the Synthesis of Colloidal Gold.

Cai, W., Xu, Q., Zhao, X., Zhu, J., Chen, H., Porous Gold Nanoparticles—CaCO3 Hybrid Material: Preparation, Characterization, and Application for Horseradish Peroxidase Assembly and Direct Electrochemistry, Chemistry of Materials, 2006, pp. 279-284, vol. 18.

Kruk, M., Asefa, T., Coombs, N., Jaroniec, M., Ozin, G., Synthesis and Characterization of Ordered Mesoporous Silicas with High Loadings of Methyl Groups, Journal of Material Chemistry, 2002, pp. 3452-3457, vol. 12.

Kruk, M., Jaroniec, M., Gas Adsorption Characterization of Ordered Organic-Inorganic Nanocomposite Materials, Chemistry of Materials, 2001, pp. 3169-3183, vol. 13.

Kresge, C., Leonowicz, M., Roth, W., Vartuli, J., Beck, J., Ordered Mesoporous Molecular Sieves Synthesized by a Liquid Crystal Template Mechanism, Letters to Nature, 1992, pp. 710-712, vol. 359.

Cheng, C. Luan, Z., Klinowski, J., The Role of Surfactant Micelles in the Synthesis of the Mesoporous Molecular Sieve MCM-41, Langmuir, 1995, pp. 2815-2819, vol. 11.

Zhao, D., Feng, J., Huo, Q., Melosh, N., Fredrickson, G., Chmelka, B., Stucky, G., Triblock Copolymer Syntheses of Mesoporous Silica with Periodic 50 to 300 Angstrom Pores, Science, 1998, pp. 548, vol. 279.

Tanev, P., Chibwe, M., Pinnavala, T., Titanium Containing Mesoporous Colecular Sieves for Catalytic Oxidation of Aromatic Compounds, Letters to Nature, 1994, pp. 321-323, vol. 368.

Tian, Z., Tong, W., Manganese Oxide Mesoporous Structures: Mixed-Valent Semiconducting Catalysts, Science, 1997, p. 926, vol. 276.

Schuth, F., Non-Siliceous Mesostructured and Mesoporous Materials, Chemistry of Materials, 2001, pp. 3184-3195, vol. 13.

Flanigen, E., Jansen, J., Introduction to Zeolite Science and Practice, Reaction Kinetics and Catalysis Letter, 1991, pp. 161-163, vol. 45, No. 1.

Chae, H., Siberio-Perez, D., Kim, J., Go, Y., Eddaoudi, M., Matzger, A., O'Keeffe, M., Yangi, O., A Route to High Surface Area, Porosity and Inclusion of Large Molecules in Crystals, Letters to Nature, 2004, pp. 523-527, vol. 427.

Hafizovic, J., Bjorgen, M., Olsbye, U., Ditezel, P., Bordiga, S., Prestipino, C., Lamberti, C., Lillerud, K, The Inconsistency in Adsorption Properties and Powder XRD Data of MOF-5 is Rationalized by Framework Interpenetration and the Presence of Organic and Inorganic Species in the Nanocavities, Journal of American Chemical Society, 2007, pp. 3612-3620, vol. 129.

Wong-Foy, A., Matzger, A., Yaghi, O., Exceptional H2 Saturation Uptake in Microporous Metal-Organic Frameworks, Journal of American Chemical Society, 2006, pp. 3494-3495, vol. 128.

Liu, B., Shioyama, H., Akita, T., Xu, Q., Metal-Organic Framework as a Template for Porous Carbon Synthesis, Journal of American Chemical Society, 2008, pp. 5390-5391, vol. 130.

Sabo, M., Henschel, A., Frode, H., Klemm, E., Kaskel, S., Solution Infiltration of Palladium into MOF-5: Synthesis, Physisorption and Catalytic Properties, Journal of Material Chemistry, 2007, pp. 3827-3832, vol. 17.

Hermes, S., Zacher, D., Baunemann, A., Woll, C., Fischer, R., Selective Growth and MOCVD Loading of Small Single Crystals of MOF-5 at Alumina and Silica Surfaces Modified with Organic Self-Assembled Monolayers, Chemistry of Materials, 2007, pp. 2168-2173, vol. 19.

Wu, Z., Xiang, H., Kim, T., Chun, M., Lee, K., Surface Properties of Submicrometer Silica Spheres Modified with Aminopropyltriethoxysilane and Phenyltriethoxysilane, Journal of Colloid and Interface Science, 2006, pp. 119-124, vol. 304.

Vallet-Regi, M., Balas, F., Arcos, D., Mesoporous Materials for Drug Delivery, Angewandte Chemie International Edition, 2007, pp. 7548-7558, vol. 46.

Fang, Q., Zhu, G., Jin, Z., Ji, Y., Ye, J., Xue, M., Yang, H., Wang, Y., Qui, S., Mesoporous Metal-Organic Framework with Rare ETB Topology for Hydrogen Storage and Dye Assembly, Angewandte Chemie International Edition, 2007, pp. 6638-6642, vol. 46.

Ren, T., Yuan, Z., Su, B., Encapsulation of Direct Blue Dye into Mesoporous Silica-Based Materials, Colloids and Surfaces A: Physiochemical and Engineering Aspects, 2007, pp. 79-87, vol. 300.

Zubieta, C., Sierra, M., Morini, M., Schulz, P., Albertengo, L., Rodriguez, M., The Adsorption of Dyes Used in the Textile Industry on Mesoporous Materials, Colloid and Polymer Science, 2008, pp. 377-384, vol. 286.

Yean, C., Kamarudin, B., Ozkan, D., Yin, L., Lalitha, P., Ismail, A., Ozsoz, M., Ravichandran, M., Enzyme-Linked Amperometric Electrochemical Genosensor Assay for the Detection of PCR Amplicons on a Streptavidin-Treated Screen-Printed Carbon Electrode, Analytical Chemistry, 2008, pp. 2774-2779, vol. 80.

Arvinte, A., Rotariu, L., Bala, C., Amperometric Low-Potential Detection of Malic Acid Using Single-Wall Carbon Nanotubes Based Electrodes, 2008, pp. 1497-1507, vol. 8.

Pan, D., Chen, J., Nie, L., Tao, W., Yao, S., An Amperometric Glucose Biosensor Based on Poly(o-Aminophenol) and Prussian Blue Films at Platinum Electrode, Analytical Biochemistry, 2004, pp. 115-122, vol. 324.

Cheng, Y., Liu, Y., Huang, J., Xian, Y., Zhang, W., Zhang, Z., Jin, L., Rapid Amperometric Detection of Coliforms Based on MWNTs/Nafion Composite Film Modified Glass Carbon Electrode, Talanta, 2008, pp. 167-171, vol. 75.

Bai, Y., Yang, H., Yang, W., Li, Y., Sun, C., Gold Nanoparticles-Mesoporous Silica Composite Used as an Enzyme Immobilization Matrix for Amperometric Glucose Biosensor Construction, Sensors and Actuators B, 2007, pp. 179-186, vol. 124.

(56) References Cited

OTHER PUBLICATIONS

Yu, J., Yu, D., Zhao, T., Zeng, B., Development of Amperometric Glucose Biosensor Through Immobilizing Enzyme in a Pt Nanoparticles/Mesoporous Carbon Matrix, Talanta, 2008, pp. 1586-1591, vol. 74.
Yao, S., Xu, J., Wang, Y., Chen, X., Xu, Y., Hu, S., A Highly Sensitive Hydrogen Peroxide Amperometric Sensor Based on MnO2 Nanoparticles and Dihexadecyl Hydrogen Phosphate Composite Film, Analytica Chimica Acta, 2006, pp. 78-84, vol. 557.
Cai, W., Xu, Q., Zhao, X., Zhu, J., Chen, H., Porous Gold Nanoparticle—CaCO3 Hybrid Material: Preparation, Characterization, and Application for Horseradish Peroxidase Assembly and Direct Electrochemistry, Chemical Materials, 2006, pp. 279-284, vol. 18.
Xu, Q., Mao, C., Liu, N., Zhu, J., Sheng, J., Direct Electrochemistry of Horseradish Peroxidase Based on Biocompatible Carboxymethyl Chitosan—Gold Nanoparticle Nanocomposite, Biosensors and Bioelectronics, 2006, pp. 768-773, vol. 22.
Su, L, Mao, L., Gold Nanoparticle/Alkanedithiol Conductive Films Self-Assembled onto Gold Electrode: Electrochemistry and Electroanalytical Application for Voltammetric Determination of Trace Amount of Catechol, Talanta, 2006, pp. 68-74, vol. 70.
Kresge, C., Leonowicz, M., Roth, W., Vartuli, J., Beck, J., Ordered Mesoporous Molecular Sieves Synthesized by a Liquid-Crystal Template Mechanism, Letters to Nature, 1992, pp. 710-712, vol. 359.
Fang, Q., Zhu, G., Jin, Z., Ji, Y., Ye, J., Xue, M., Yang, H., Wang, Y., Qiu, S., Mesoporous Metal-Organic Framework with Rare ETB Topology for Hydrogen Storage and Dye Assembly, Angewandte Chemie International Edition, 2007, pp. 6638-6642, vol. 46.
Asefa, T., Maclachlan, M., Coombs, N., Ozin, G., Periodic Mesoporous Organosilicas with Organic Groups Inside the Channel Walls, Letters to Nature, 1999, pp. 867-871, vol. 402.
Yu, A., Liang, Z., Cho, J., Caruso, F., Nanostructured Electrochemical Sensor Based on Dense Gold Nanoparticle Films, Nano Letters, 2003, pp. 1203-1207, vol. 3.
Chen, S., Carroll, D., Synthesis and Characterization of Truncated Triangular Silver Nanoplates, Nano Letters, 2002, pp. 1003-1007, vol. 2.
Metraux, G., Cao, Y., Jin, R., Mirkin, C., Triangular Nanoframes Made of Gold and Silver, Nano Letters, 2003, pp. 519-522, vol. 3.
Kavan, L, Gratzel, M., Gilbert, S., Klemenz, C., Scheel, H., Electrochemical and Photoelectrochemical Investigation of Single-Crystal Anatase, Journal of American Chemical Society, 1996, pp. 6716-6723, vol. 118.
Klimov, V., Mechanisms for Photogeneration and Recombination of multiexcitons in Semiconductor Nanocrystals: Implications for Lasing and Solar Energy Conversion; Journal of Physical Chemistry B, 2006, pp. 16827-16845, vol. 110.
Joo, J., Na, H., Yu, T., Yu, J., Kim, Y., Wu, F., Zhang, J., Hyeon, T., Generalized and Facile Synthesis of Semiconducting Metal Sulfide Nanocrystals, Journal of American Chemical Society, 2003, pp. 11100-11105, vol. 125
Erdem, A., Nanomaterial-based Electrochemical DNA Sensing Strategies, Talanta, 2007, pp. 318-325, vol. 74.
Liu, G., Lin, Y., Nanomaterial Labels in Electrochemical Immunosensors and Immunoassays, Talanta, 2007, pp. 308-317, vol. 74.
Jin, R., Cao, Y., Mirkin, C., Kelly, K., Schatz, G., Zheng, J., Photoinduced Conversion of Silver Nanospheres to Nanoprisms, Science, 2001, pp. 1901-1903, vol. 294.
Ravidran, S., Chaudhary, S., Colburn, B., Ozkan, M., Ozkan, C., Covalent Coupling of Quantum Dots to Miltiwalled Carbon Nanotubes for Electronic Device Applications, Nano Letters, 2003, pp. 447-453, vol. 3, No. 4.
Hu, J., Zhang, Y., Liu, B., Liu, J., Zhou, H., Xu, Y., Jiang, Y., Yang, Z., Tian, Z., Synthesis and Properties of Tadpole-Shaped Gold Nanoparticles, Journal of American Chemical Society, 2004, pp. 9470-9471, vol. 126.
Shen, Q., Sato, T., Hashimoto, M., Chen, C., Toyoda, T., Photoacoustic and Photoelectrochemical Characterization of CdSe-sensitized TiO2 Electrodes Composed of Nanotubes and Nanowires, Thin Solid Films, 2006, pp. 299-305, vol. 499.
Hao, E., Bailey, R., Schatz, G., Hupp, J., Li, S., Synthesis and Optical Properties of "Branched" Gold Nanocrystals, Nano Letters, 2004, pp. 327-330, vol. 4, No. 2.
Narayanan, R., El-Sayed, M., Effect of Nanocatalysis in Colloidal Solution on the Tetrahedral and Cubic Nanoparticle SHAPE: Electron-Transfer Reaction Catalyzed by Platinum Nanoparticles, Journal of Physical Chemistry B, 2004, pp. 5726-5733, vol. 108.
Milliron, D., Hughes, S., Cui, Y., Manna, L., Li, J., Wang, L., Alivisatos, A., Colloidal Nanocrystal Heterosructures with Linear and Branched Topology, Letters to Nature, 2004, pp. 190-195, vol. 430.
Gaikwad, A., Verschuren, P., Kinge, S., Rothenberg, G., Eiser, E., Matter of Age: Growing Anisotropic GOld Nanocrystals in Organic Media, Physical Chemistry Chemical Physics, 2008, pp. 951-956, vol. 10.
Link, S., El-Sayed, M., Spectral Properties and Relaxation Dynamics of Surface Plasmon Electronic Oscillations in Gold and Silver Nanodots and Nanorods, Journal of Physical Chemistry B, 1999, pp. 8410-8426, vol. 103.
Yu, Y., Chang, S., Lee, C., Wang, C., Gold Nanorods: Electrochemical Synthesis and Optical Properties, The Journal of Physical Chemistry B, 1997, pp. 6661-6664, vol. 101, No. 34.
Peng, X., Manna, L., Yang, W., Wickham, J., Scher, E., Kadavanich, A., Alivisatos, A., Shape Control of CdSe Nanocrystals, Letters to Nature, 2000, pp. 59-61, vol. 404.
Jana, N., Gearheart, L., Murphy, C., Wet Chemical Synthesis of High Aspect Ratio Cylindrical Gold Nanorods, Journal of Physical Chemistry B, 2001, pp. 4065-4067, vol. 105.
Sun, Y., and Xia, Y., Shape-Controlled Synthesis of Gold and Silver Nanoparticles, Science, 2002, pp. 2176-2179, vol. 298.
Maillard, M., Giorgio, S., Pileni, M., Silver Nanodisks, Advanced Materials, 2002, pp. 1084-1086, vol. 15.
Maillard, M., Huang, P., Brus, L., Silver Nanodisk Growth by Surface Plasmon Enhanced Photoreduction of Adsorbed [Ag+], Nano Letters, 2003, pp. 1611-1615, vol. 3, No. 11.
Shi, W., Zeng, H., Sahoo, Y., Ohulchanskyy, T., Ding, Y., Wang, Z., Swihart, M., Prasad, R, A General Approach to Binary and Ternary Hybrid Nanocrystals, Nano Letters, 2006, pp. 875-881, vol. 6, No. 4.
Shi, W., Sahoo, Y., Zeng, H., Ding, Y., Swihart, M., Prasad, P., Anisotropic Growth of PbSe Nanocrystals on Au-Fe3O4 Hybrid Nanoparticles, Advanced Materials, 2006, pp. 1889-1894, vol. 18.
Hartgerink, J., Beniash, E., Stupp, S., Self-Assembly and Mineralization of Peptide-Amphiphile Nanofibers, Science, 2001, pp. 1684-1688, vol. 294.
Steven, A., Roberts, C., Hay, J., Bisher, M., Pun, T., Trus, B., Hexavalent Capsomers of Herpes Simplex Virus Type 2: Symmetry, Shape, Dimensions, and Oligomeric Status, Journal of Virology, 1986, pp. 578-584, vol. 57, No. 2.
Chen, T., Zhang, Z., Glotzer, S., Simulation Studies of the Self-Assembly of Cone-Shaped Particles, Langmuir, 2007, pp. 6598-6605, vol. 23.
Park, S., Lim, J., Chung, S., Mirkin, C., Self-Assembly of Mesoscopic Metal-Polymer Amphiphiles, Science, 2004, pp. 348-351, vol. 303.
Manoharan, V., Elsesser, M., Pine, D., Dense Packing and Symmetry in Small Clusters of Microshperes, Science, 2003, pp. 483-487, vol. 301.
Wang, W., Gu, B., Liang, L., Hamilton, W., Fabrication of Near-Infared Photonic Crystals Using Highly-Monosidpersed Submicrometer SiO2 Spheres, Journal of Physical Chemistry B, 2003, pp. 12113-12117, vol. 107.
De Dood, M., Berkhout, B., Van Kats, C., Polman, A., Van Blaaderen, A., Scid-Based Syntheses of Monodisperse Rare-Earth-Doped Colloidal Si02 Spheres, Chemistry of Materials, 2002, pp. 2849-2853, vol. 14.
Ibisate, M., Zou, Z., Xia, Y., Arresting Fixing, and Separating Dimers Composed of Uniform Silica Colloidal Spheres, Advanced Functional Materials, 2006, pp. 1627-1632, vol. 16.

(56) References Cited

OTHER PUBLICATIONS

Kim, K., Webster, S., Levi, N., Carroll, D., Pinto, M., Schanze, K., Luminescent Core-Shell Photonic Crystals from Poly (Phenylene Ethnlene) Coated Silica Spheres, Langmuir, 2005, pp. 5207-5211, vol. 21.

Lee, S. Yi, G., Yang, S., High-Speed Fabrication of Patterned Colloidal Photonic Structures in Centrifugal Microfluidic Chips, Lab on a Chip, 2006, pp. 1171-1177, vol. 6.

Stober, W., Fink, A., Bohn, E., Controlled Growth of Monodisperse Silica Spheres in the Micron Size Range, Journal of Colloidal and Interface Science, 1968, pp. 62-69, vol. 26.

Leinweber, F., Tallarek, U., Chromatographic Performance of Monolithic and Particulate Stationary Phases Hydrodynamics and Adsorption Capacity, Journal of Chromotography A, 2003, pp. 207-228, vol. 1006.

Haruta, M., Size and Support Dependancy in the Catalysis of Gold, Catalysis Today, 1997, pp. 153-166, vol. 36.

Velikov, K., Zegers, G., Van Blaaderen, A., Synthesis and Characterization of Large Colloidal Silver Particles, Langmuir, 2003, pp. 1384-1389, vol. 19.

Ding, S. Qian, W Tan, Y. Wang, Y. In-Situ Incorporation of Gold Nanoparticles of Desired Sizes into Three-Dimensional Macroporous Matrixes, Langmuir, 2006, pp. 7105-7108, vol. 22.

Zhu, Y., Chen, H., Wang, Y., Li, Z., Cao, Y., Chi, Y., Mesoscopic Photonic Crystals Made of TiO2 Hollow Spheres Connected by Cylindrical Tubes, Chemistry Letters, 2006, pp. 756-757, vol. 35, No. 7.

Ruhl, T., Spahn, P., Hermann, C., Jamois, C., Hess, O., Double-Inverse-Opal Photonic Crystals: The Route to Photonic Bandgap Switching, Advanced Functional Materials, 2006, pp. 885-890 vol. 16.

Chiappini, A., Armellini, C., Chiasera, A., Ferrari, M., Jestin, Y., Mattarelli, M., Montaga, M., Moser, E., Conti, G., Pelli, S., Righini, G., Concalves, M., Almeida, R., Design of Photonic Structures by Sol-Gel-Derived Nanospheres, Hournal of Non-Crystalline Solids, 2007, pp. 674-678, vol. 353.

Chen, J., Von Freymann, G., Choi, S., Kitaev, V., Ozin, G., Slow Photons in the Fast Lane in Chemistry, Journal of Material Chemistry, 2005, pp. 369-373, vol. 18.

Silver, J., Ireland, T., Withnall, R., Facile Method of Infilling Photonic Silica Templates with Rare Earth Element Oxide Phosphor Precursors, Journal of Materials Research, 2004, pp. 1656-1661, vol. 19, No. 6.

Lopez, C., Three Dimensional Photonic Bandgap Materials: Semiconductors for Light, Journal of Optics A: Pure and Applied Optics, 2006, pp. R1-R14, vol. 8.

Sinitskii, A., Photonic Crystals: New Ideas and Future Prospects (SPIE Photonics Europe 2006 Conference), Inorganic Materials, 2006, pp. 1404-1407, vol. 42, No. 12.

Shi, Y., Asefa, T., Tailored Core-Shell-Shell Nanostructures: Sandwiching Gold Nanoparticles Between Silica Cores and Tunable Silica Shells, Langmuir, 2007, pp. 9455-9462, vol. 23.

Aslan, K., Wu, M., Lakowicz, J., Geddes, C., Metal Enhanced Fluorescence Solution-Based Sensing Platform 2: Fluorescent Core-Shell Ag@SiO2 Nanoballs, Journal of Fluorescence, 2007, pp. 127-131, vol. 17.

Sikorski, Y., Rablau, C., Dugan, M., Said, A., Bado, P., Beholz, L., Fabrication and Characterization of Microstructures with Optical Quality Surfaces in Fused Silica Glass Using Femtosecond Laser Pulses and Chemical Etching, Applied optics, 2006, pp. 7519-7523, vol. 45, No. 28.

Liu, R., Shi, Y., Wan, Y., Meng, Y., Zhang, F., Gu, D., Chen, Z., Tu, B., Zhao, D., Triconstituent Co-Assembly to Ordered Mesostructured Polymer-Silica and Carbon-Silica Nanocomposites and Large-Pore Mesoporous Carbons with High Surface Areas, Journal of American Chemical Society, 2006, p. 11652, vol. 128.

Jin, Z., Wu, C., Ma, H., Xu, N., Wang, Y., The Effects of Diffusion Coefficient on the Etching Process of Sacrificial Oxide Layers, Thin Solid Films, 2007, pp. 3065-3072, vol. 515.

Kumar, A., Pushparaj, V., Murugesan, S., Viswanathan, G., Nalamasu, R., Linhardt, R., Nalamasu, O., Ajayan, P., Syntheses of Silica-Gold Nanocomposites and Their Porpos Nanoparticles by an In-Situ Approach, Langmuir, 2006, pp. 8631-8634, vol. 22.

\* cited by examiner

The full images with scale bars are shown on Fig. 2.

(A) Si450-KCN-H4

(B) Si450-KCN-H8

(C) Si450-KOH-H8

CORRUGATED AND NANOPOROUS MICROSTRUCTURES AND NANOSTRUCTURES, AND METHODS FOR SYNTHESIZING THE SAME

RELATED APPLICATION DATA

The present application claims priority to U.S. provisional patent application No. 61/099,641, filed Sep. 24, 2008; all of the foregoing patent-related documents are hereby incorporated by reference herein in their respective entireties.

BACKGROUND OF THE INVENTION

1. Field of Invention

The present invention relates generally to microstructures and nanostructures, and, more particularly, to corrugated and nanoporous microspheres/nanospheres, and methods of synthesizing the same.

2. Description of Prior Art

The synthesis of inorganic nanomaterials with controllable sizes, shapes, and structures has become increasingly important in modern inorganic materials chemistry today. These materials exhibit a wide range of unique physical, chemical, surface, electronic and optical properties associated with their sizes and shapes. They thus have potential for catalysis, separation, chromatography, surface enhanced Raman spectroscopy and biological diagnostic applications; as well as for fabrication of various electrical, photovoltaic, photonics, magnetic, microelectronics, chemical sensor and optical devices. Thus far, most synthesis methods have concentrated on smooth, spherical and symmetrical nanomaterials, mainly because their synthesis is simpler and their size is easier to control. Nanoparticles with non-spherical or non-symmetrical shapes are known to possess several properties that are unique compared to their spherical counterparts, while their controlled synthesis is often met with considerable challenges. For instance, the catalytic activity of noble metal nanocrystals depends on their shapes in addition to their sizes. Unique physical properties, such as optical and electronic as well as magnetic flux trapping and photoluminescence, can also be obtained from shaped and anisotropic nanomaterials. Furthermore, it was proven that non-symmetrical and non-spherical inorganic, organic, and biological nanostructures can self-aggregate into rather unique structures that their corresponding spherical counterparts are not capable of forming Consequently, the self-aggregates from non-spherical nanomaterials can produce unusual properties as well as unique "hard templates" that can be useful for generating other asymmetric nanostructures and photonics band gap materials for microphotonics and microelectronics applications.

The Stöber synthesis, which was first reported in 1963, has long been the method of choice for making silica microspheres. The silica microspheres that result from the Stöber method have rather symmetrical or spherical shape and a smooth surface. Many researchers have demonstrated that these silica microspheres have potential applications in areas ranging from chromatography to catalysis. For instance, by using the silica microspheres, various metal supported catalysts, metal nanoshells for biological applications, and hollow and core-shell nanomaterials have been successfully synthesized. The recent advances in the field of photonics have also resulted in renewed interest in the development of synthetic methods to monodisperse silica microspheres and their self-assembly into opal and inverse opal structures. Silica microspheres, particularly those with monodisperse size, can pack into perfect colloidal crystals, which can then be infiltrated with various precursors to produce so-called photonics band-gap materials. The resulting photonics band gap materials have interesting optical light trapping properties that are useful for photonics applications. However, since the silica microspheres synthesized by the Stöber method or some variations of the Stöber method often have smooth surfaces, the complete infiltration of their perfectly packed colloidal crystal structures with monomers, chromophores, polymers and other molecules remains to be problematic. Consequently, the formation of defect sites and void spaces in the resulting opal and inverse opal structures as well as in photonics band gap materials is often too common.

Recently, upon etching gold nanoparticles (AuNP) sandwiched between a silica microsphere and a silica shell with aqueous KCN solution, it has been observed that a higher concentration of KCN solution etches the silica shell and produces some silica/AuNP/silica core-shell-shell nanospheres containing a corrugated surface. Furthermore, while the etching of solid glass substrates and metal oxide microspheres, including silica microspheres, by various strong bases and HF solutions is already known, it has been widely used for nanopatterning solid state substrates or for complete dissolution of silica to create hollow nanostructures. For instance, by utilizing the commonly used etchants such as HF solutions or strongly basic KOH and NaOH solutions, complete dissolution of silica nanostructures was achieved. Silica in strongly basic solutions undergoes quick dissolution via the hydrolysis of its siloxane bonds while silica in HF solutions form soluble tetrafluosilicate species. In addition to these wet-etching processes, other physical methods involving etching with plasma, molecular beam epitaxy (MBE), and laser ablation can be used to etch silica or other metal oxides. By using the latter methods, many nanoelectronics and optical devices have also been fabricated.

SUMMARY OF THE INVENTION

In accordance with an embodiment of the present invention, the fact that it has been observed that a higher concentration of KCN solution etches the silica shell and produces some silica/AuNP/silica core-shell-shell nanospheres containing a corrugated surface is interesting considering the fact that KCN solution was previously reported to etch noble metals such as silver and gold in the presence of silica without touching the silica structure. Although previous work indeed proved that a higher concentration of KCN solution produces a large enough [OH$^-$] concentration that can also etch the silica surface, systematic studies involving controlled etching of various sized silica microspheres by basic solutions into different corrugated and hollow microspheres and the potential applications of the resulting etched microspheres have not been demonstrated by the prior art.

It is therefore a principal object and an advantage of the present invention to provide corrugated and nanoporous microspheres.

It is another object and advantage of the present invention to provide corrugated and nanoporous microspheres via controlled etching of smooth, spherical microspheres.

It is a further object and advantage of the present invention to provide corrugated and nanoporous silica microspheres, and other types of metal oxide microspheres such as titania ($TiO_2$) microspheres and the like.

It is another object and advantage of the present invention to provide corrugated and nanoporous silica microspheres via controlled etching of smooth, spherical silica microspheres, and corrugated and nanoporous metal oxide microspheres, such as titania ($TiO_2$) microspheres, via controlled etching of smooth, spherical metal oxide microspheres.

In accordance with the foregoing objects and advantages, an embodiment of the present invention provides corrugated and nanoporous silica microspheres. In accordance with an embodiment of the present invention, corrugated and nanoporous silica microspheres were synthesized by the controlled etching of smooth, spherical silica microspheres with aqueous KCN or KOH solution.

In accordance with an embodiment of the present invention, corrugated and nanoporous silica microspheres were synthesized by simple controlled etching of smooth spherical silica microspheres of various sizes with aqueous KCN or KOH solution. The smooth silica microspheres were prepared by the Stöber method. The structure and morphology of the etched microspheres were controlled by varying the type and concentration (pH value) of the etchants and the etching time. Upon etching the original silica microspheres with a higher concentration of etchant for a longer time, highly corrugated and hollow silica microspheres were obtained. Shorter etching time and a lower concentration of etchant have resulted in only moderately corrugated microspheres. Comparative studies revealed that the etching with KCN solution proceeds more slowly due to the milder concentration of $OH^-$ ions it generates compared to a similar concentration of KOH solution. By optimizing the etching process, silica microspheres with increased adsorption capacity for chemicals such as rhodamine 6G can be obtained. By encapsulating gold nanoparticles and horseradish peroxidase into the etched microspheres having optimized corrugated structures and then casting the resulting nanocomposite materials on a glassy carbon electrode, sensitive electrochemical biosensors for the detection of micromolar concentrations of $H_2O_2$ were fabricated. The correlations between the microspheres' size, the etchant's concentration and the etching time with the structures and shapes of the etched microspheres, their adsorption properties to chemicals, and their potential in biosensing application were established. The synthetic method also proved to be applicable in producing corrugated/hollow titania microspheres. This controlled etching synthetic method to produce corrugated metal oxide microspheres is versatile and is useful for controlling nanomaterials' structure and morphology, enhancing their surface area and adsorption capacity of chemicals and drug molecules, as well as making sensitive electrochemical biosensors.

BRIEF DESCRIPTION OF THE DRAWINGS

The present invention will be more fully understood and appreciated by reading the following Detailed Description in conjunction with the accompanying drawings, in which.

after etching with 1 mL of higher KCN concentration (0.03 M, pH=11.00) for (A) 4, (B) 13 and (C) 23 h under static condition, according to an embodiment of the present invention.

FIGS. 13A-13E show $N_2$ gas absorption isotherms of as-prepared silica microspheres Si450 and various corresponding etched microspheres Si450-KCN—H4, Si450-KCN—H8, Si450-KOH—H4 and Si450-KOH—H8, according to an embodiment of the present invention.

Figure 14A:
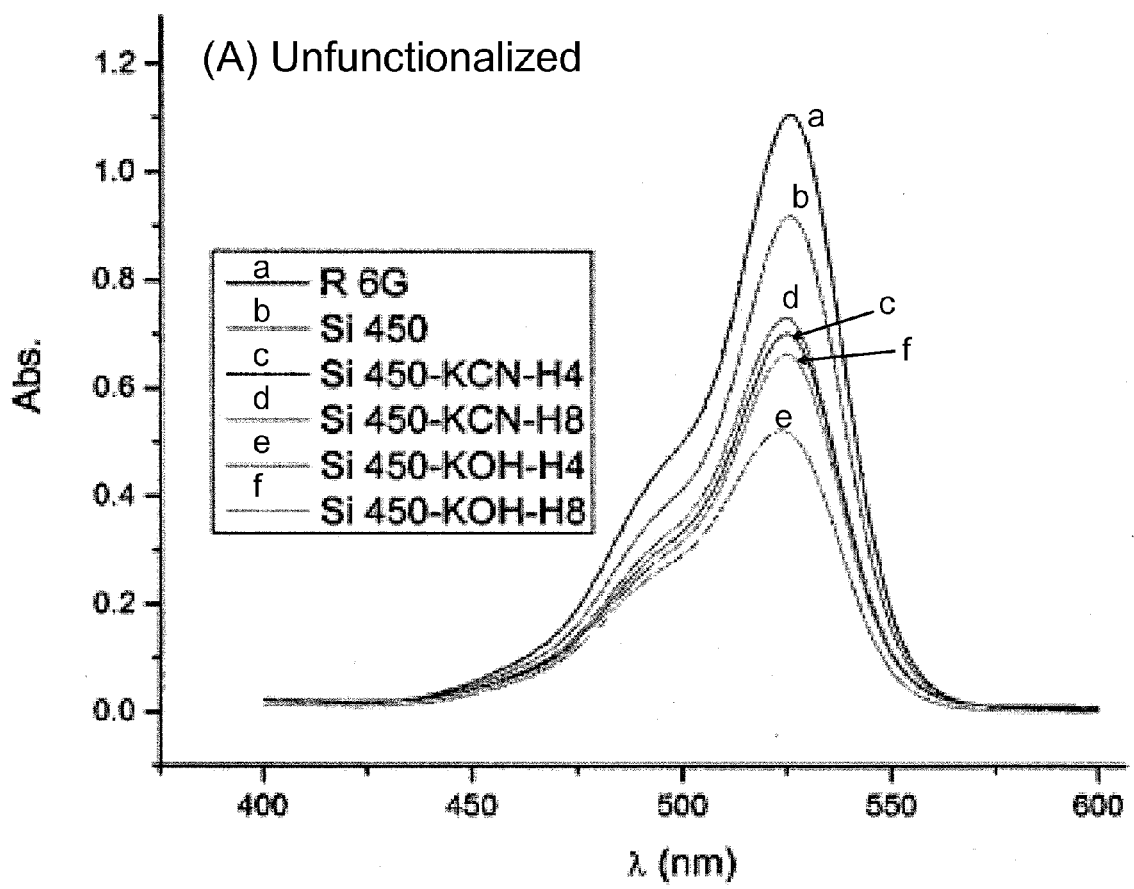
Figure 14B:
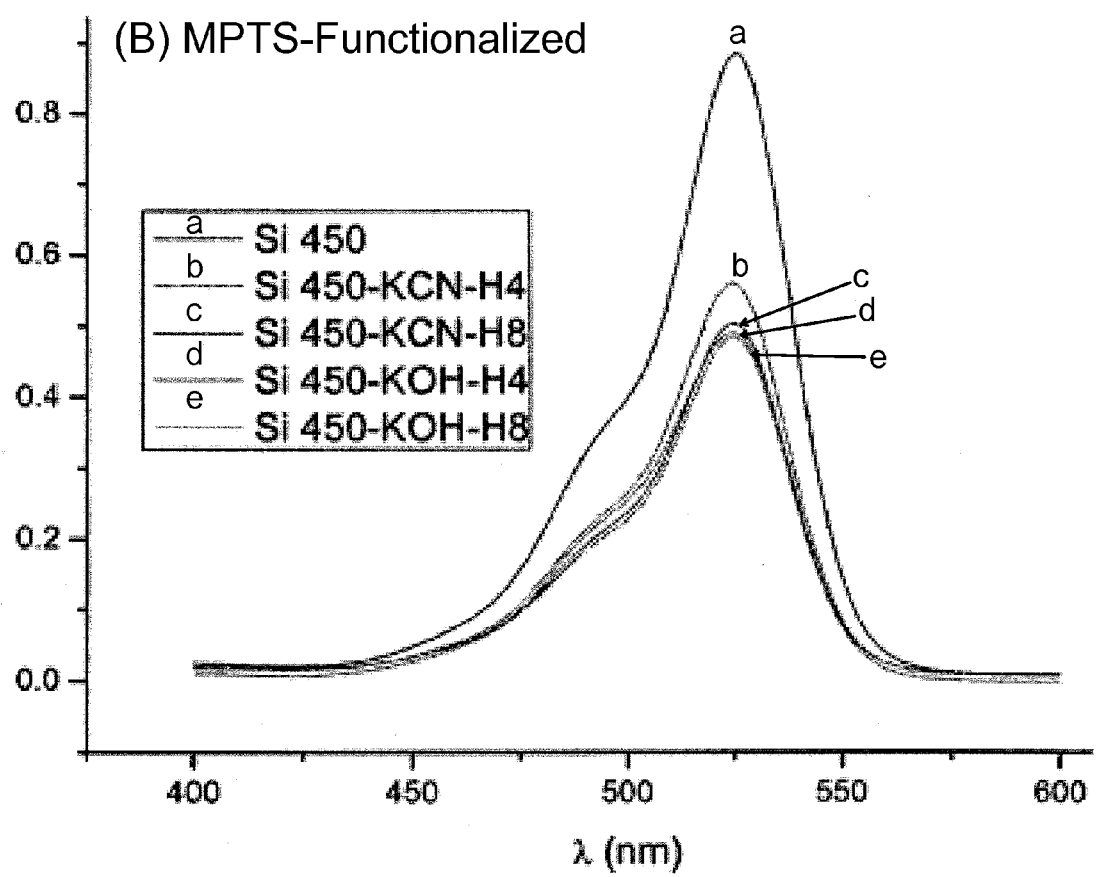
Figure 14C:
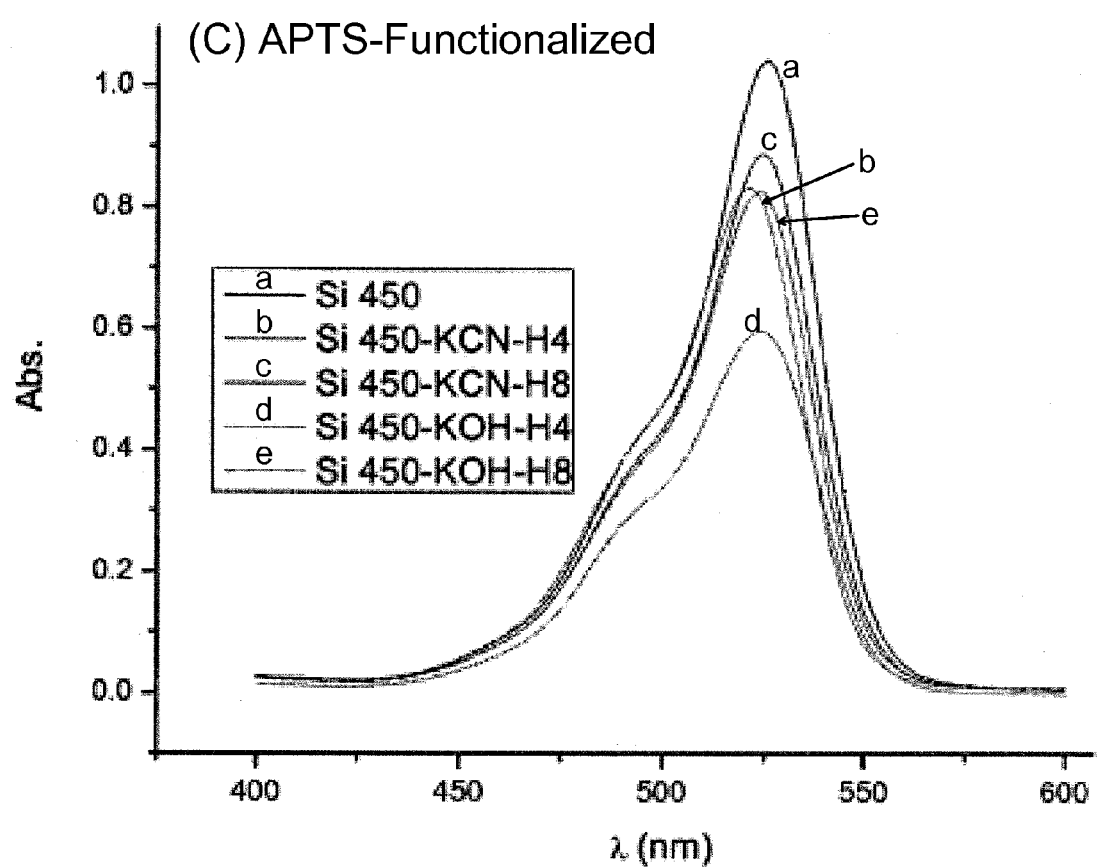

FIGS. 14A-14C show UV-vis absorption spectra of rhodamine 6G (R6G) in the supernatant after adsorption of a R6G solution by various unetched and etched silica microspheres Si450 under various conditions: (A) unfucntionalized samples; (B) after functionalization of their surface with 3-aminopropyl groups; and (C) after functionalization of their surface with 3-mercaptopropyl groups, according to an embodiment of the present invention. All the experiments were conducted under the same condition and by using the same mass of samples.

Figure 15:
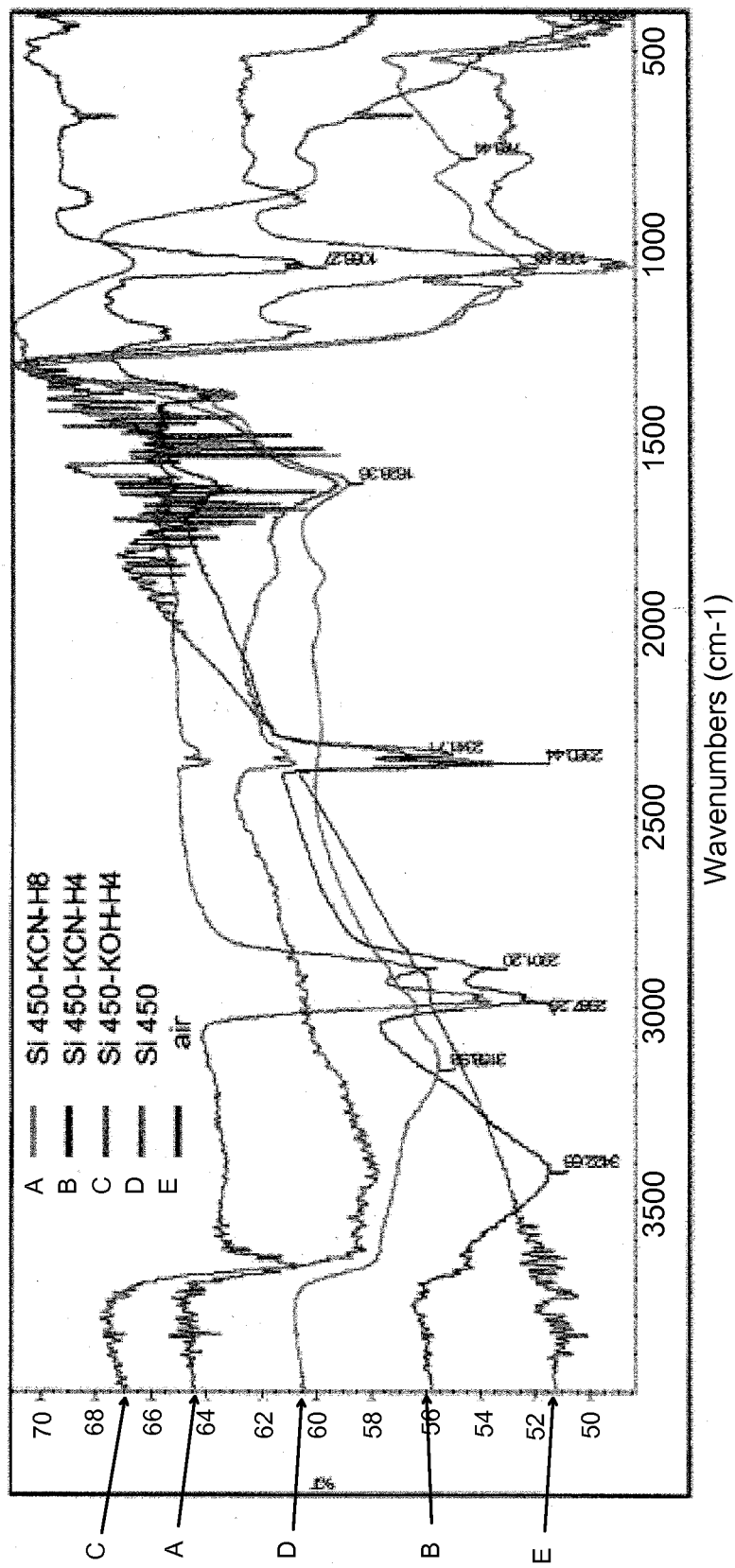

FIG. 15 shows FT-IR spectra of silica microspheres of average diameter of 450 nm (Si450) before and after etching with KCN and KOH solution.

FIGS. 16A-16C show TEM images of gold anchored (A) Si450-KCN—H4; (B) Si450-KCN—H8; and (C) Si450-KOH—H8 microspheres, according to an embodiment of the present invention.

Figure 17A:
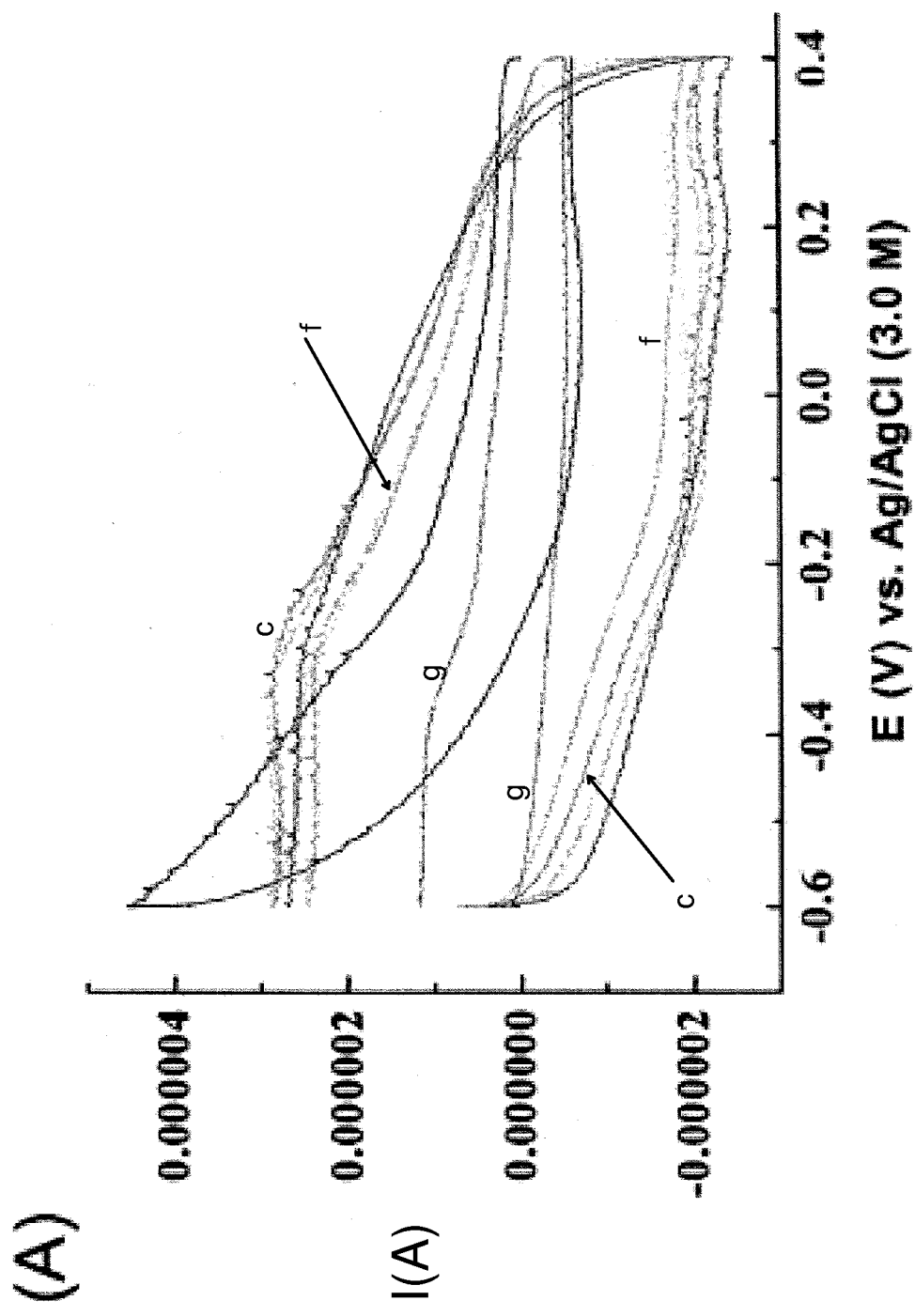
Figure 17B:
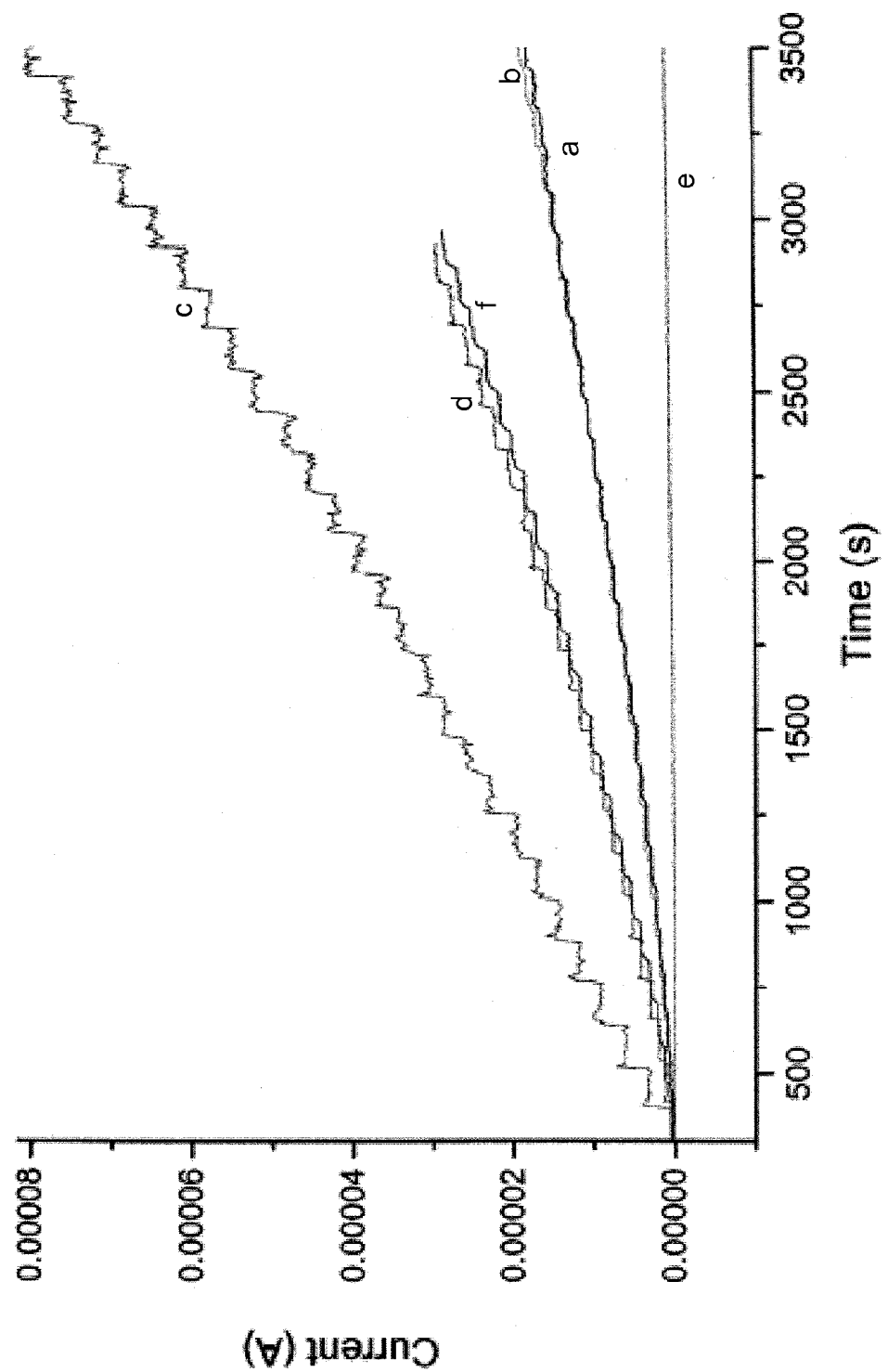

FIGS. 17A-17B show (A) cyclic voltammetry curves of glassy carbon (GC) electrodes modified with: (a) Si450-AuNP; modified with various etched $SiO_2$—AuNP-HRP microsphere samples in PBS (pH=7.2) including (b) Si450-KOH—H8-AuNPs-HRP; (c) Si450-KOH—H4-AuNP-HRP; (d) Si450-KCN—H8-AuNP-HRP; (e) Si450-KCN—H4-AuNP-HRP; (f) Si450-AuNP-HRP; and (g) Si450-KCN-HR-HRP (no AuNPs), according to an embodiment of the present invention. Scan rate: 100 mV/s. (B) Typical steady-rate current response of GC electrodes modified with various etched $SiO_2$—AuNP-HRP microsphere samples on successive injection of 50 μL (250 mM) of $H_2O_2$ into 10 mL PBS (pH 7.2) under stirring, according to an embodiment of the present invention. The graphs show for samples (a) Si450-KCN—H4; (b) Si450-KCN—H8; (c) Si450-KOH—H4; (d) Si450-KOH—H8; (e) Si-450-KCN—H4(no AuNPs); and (f) Si450, according to an embodiment of the present invention. Applied potential: –0.35 V.

FIGS. 18A-18B show TEM images of $TiO_2$ microspheres with ~400 nm diameter after etching with 1 mL of high KOH concentration (0.03 M, pH=12.60) for (A) 4 and (B) 8 h, according to an embodiment of the present invention.

DETAILED DESCRIPTION

Reference will now be made in detail to the present preferred embodiments of the invention, examples of which are illustrated in the accompanying drawings.

In accordance with an embodiment of the present invention, the synthesis of new classes of corrugated and nanoporous silica microspheres was achieved by controlled etching of various sizes of silica nanospheres (microspheres and nanospheres are used interchangeably herein) with a KCN and/or KOH solution (as shown in the Examples, infra). The structures and morphology of the etched microspheres were controlled by varying the sizes of the original silica microspheres (e.g., 50-600 nm), the concentration of KCN or KOH solutions, and the etching time.

Figure 1:
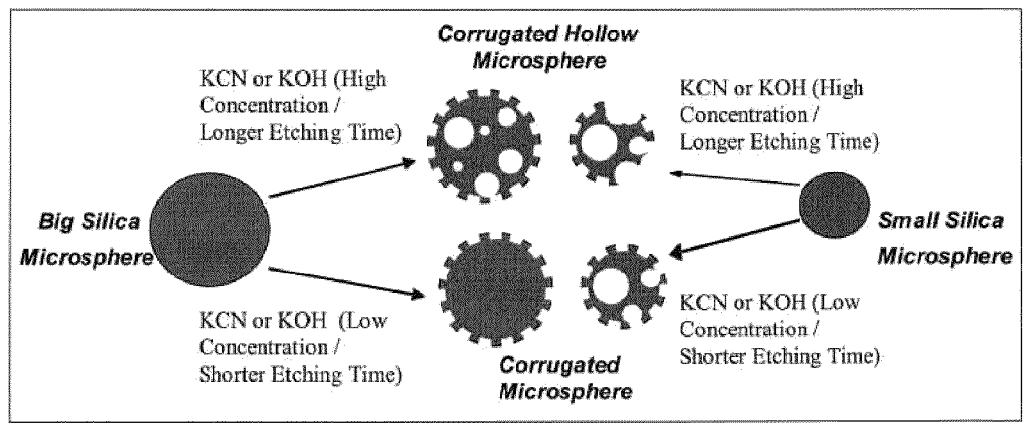
FIG. 1 shows synthesis of corrugated, nanoporous and hollow silica microspheres by controlled etching of silica microspheres, according to an embodiment of the present invention.

In accordance with an embodiment of the present invention, a simple wet synthetic method for synthesizing corrugated, nanoporous and hollow silica microspheres, which involve controlled etching of spherical silica microspheres with dilute aqueous KOH or KCN solutions (see FIG. 1), is provided. As shown in the Examples below, the novel method of synthesizing corrugated/hollow silica microspheres by controlled wet-etching of silica microspheres was demonstrated by etching different size spherical silica microspheres consisting of fairly smooth surfaces with different concentrations of KOH and KCN solutions for various periods of time. The etching resulted in slightly corrugated, highly corrugated, or hollow/corrugated microspheres depending on the type of etchant, its concentration, the etching time, and the size of the original microspheres. The resulting etched microspheres have robust corrugated surface structure and morphology and are proven more efficient for adsorption of chemicals, enzymes and nanoparticles compared to the original unetched microspheres. Furthermore, the resulting etched microspheres have been found to be suitable as a platform for the fabrication of electrochemical biosensors. The biosensing application was demonstrated by anchoring horseradish peroxidase and gold nanoparticles onto the etched microspheres, then by placing the resulting nanocomposite materials onto a glassy carbon electrode, and finally by electrochemically detecting micromolar concentration of $H_2O_2$ with the biosensor. The etched microspheres gave a biosensor with better sensitivity than the corresponding as-prepared, unetched samples. The novel synthesis method to corrugated microspheres provided herein is simple, versatile and is proved to be applicable to other metal oxide microspheres such as titania microspheres.

Advantages of the invention are illustrated by the following Examples. However, the particular materials and amounts thereof recited in these examples, as well as other conditions and details, are to be interpreted to apply broadly in the art and should not be construed to unduly restrict or limit the invention in any way.

The materials and reagents referred to in the following Examples such as tetraethoxysilane (TEOS), 3-aminopropyltriethoxysilane (APTS), sodium citrate, rhodamine 6G, potassium cyanide (97%), sodium hydroxide, tetrahydrofuran (THF), horseradish peroxidase (HRP), phosphate buffer solution (PBS) (pH=7.2), titanium butoxide and sodium borohydride were obtained from Sigma-Aldrich and they were used as received with no further purification. Ammonia solution (30%), hydrogen peroxide solution (30%) and potassium chloride were obtained from Fisher Scientific. 3-Mercaptoproyltriethoxysilane (MPTS) was purchased from Gelest. Hydrogen tetrachloroaurate (III) was obtained from Strem Chemicals. Anhydrous ethanol was received from Pharmco AAPR. A glassy carbon electrode (GCE), diamond suspensions (3 μm and 1 μm) and alumina suspension (0.05 μm) were obtained from BAS, Inc. As should be understood by those skilled in the art, KCN should not be mixed with acids as it may form toxic HCN gas.

If not noted elsewhere within the following Examples, the instrumentation used and the measurements taken referred to in the following Examples were used and taken, respectively, pursuant the following: UV-Vis was measured with a LAMBDA 950 UV/Vis/NIR spectrophotometer (PerkinElmer). The BET gas adsorptions were measured with Micromeritics Tristar 3000 volumetric adsorption analyzer at 77 K by following a previously reported procedure. The TEM images were taken by using an FEI Tecnai T-12 S/TEM instrument. All electrochemical experiments were performed on a potentiostat PAR-263 A (Princeton Applied Research) with powersuite software. FT-IR spectra were obtained on Nicolet IR200 FT-IR spectrometer (Thermo Fisher Scientific).

EXAMPLE 1

This Example describes the synthesis of silica microspheres of various sizes. The synthesis of the various sized silica microspheres, was carried out following a Stöber method. In particular, silica microspheres of average sized diameters 450, 250, and 110 nm (see FIG. 2) were synthesized by the Stöber method.

Briefly, 2.92 g of tetraethoxysilane (TEOS) was added into 5 mL of 5 M ammonia solution in 50 mL ethanol and 1.8 g of water under stirring to hydrolyze TEOS. After 12 h of stirring, the solution was centrifuged and the precipitate was washed twice with ethanol and dried in a desiccator under vacuum resulting in silica microspheres of 450 nm in diameter. The as-prepared silica microspheres of diameters of 450 nm diameter were named Si450. The sizes of the silica spheres were changed by varying the concentration of the base in the solution. Silica microspheres with diameters of 110 and 250 nm were also synthesized by following the procedure above but by using 2.0 and 3.5 mL of ammonia solution, respectively. This has resulted in as-prepared silica microspheres that were labeled as Si110 and Si250, respectively.

Figure 2:
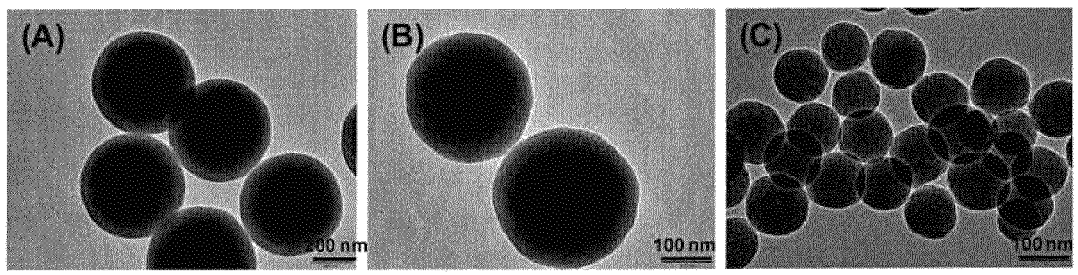
FIGS. 2A-2C show TEM images of as-prepared silica microspheres with an average diameter of (A) ~450, (B) ~250 and (C) ~110 nm, which are labeled as Si450, Si250 and Si110, respectively, according to an embodiment of the present invention.
Figure 3:
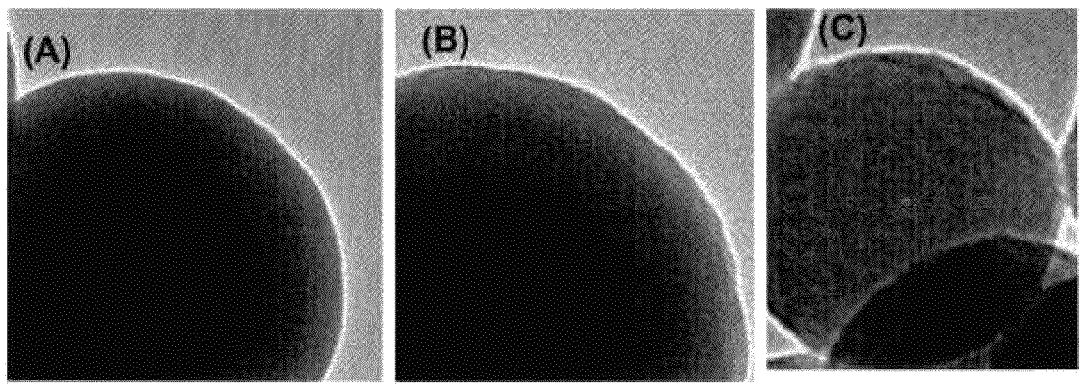
FIGS. 3A-3C show enlarged TEM image of silica microspheres of average diameter of (A) ~450, (B) ~250 and (C) ~110 nm and that are labeled as Si450, Si250 and Si110, respectively, according to an embodiment of the present invention.

The results showed that the resulting silica microspheres have a rather smooth surface and spherical shape (FIG. 2). It is worth noting that as the size of the microspheres decreased, their surface became slightly rugged (see FIG. 3) and their polydispersity increased (FIG. 2).

EXAMPLE 2

This Example relates to the synthesis of corrugated or nanoporous silica microspheres by etching the various sized silica microspheres obtained in Example 1. These silica microspheres having different diameters were etched with various concentrations of aqueous KCN or KOH solutions for different periods of time under mechanical shaking or under static condition.

The synthesis of corrugated and hollow microspheres by etching the spherical silica microspheres was carried out in aqueous potassium cyanide (KCN) and aqueous potassium hydroxide (KOH) solutions. In the case of KCN solution, a 0.03 M concentration (pH=11.00 or "high KCN concentration") and a 0.006 M (pH=10.20 or "low KCN concentration") were used. For comparison purposes, a 0.03 M KOH solution with a pH value of 12.60 (high KOH concentration) and a KOH solution with a pH value of 11.00 (low KOH concentration), which has the same pH as that of the 0.03 M KCN solution, were used as etchant. In a typical etching synthesis, 100 µl of the 450 nm silica microspheres (Si450) that were suspended in water with a concentration of 10 mg/mL was mixed with 1 mL of 0.03 M KCN solution ("high KCN concentration") or 0.03 M KOH solution ("high KOH concentration") in a falcon tube. The mixture was stirred on a shaker for 4 h. The etched silica microspheres were collected by centrifugation and washed with deionized water three times prior to drying in a desiccator under vacuum. The resulting samples from etching with the KCN and KOH solutions for 4 h were labeled as Si450-KCN—H4 and Si450-KOH—H4, respectively. This labeling was chosen to indicate the size of the silica microspheres, the type of etchant, its concentration and the etching time used in the synthesis, where "H" stands for high concentration and "4" stands for 4 h etching time. The other etched samples were also labeled accordingly. For instance, the silica microspheres, Si450, etched in low concentration (0.006 M) of KOH or KCN for 8 h were labeled as Si450-KOH-L8 and Si450-KCN-L8, respectively, where "L" was used to indicate the lower concentration of etchant.

The results showed etched microspheres having different types of structures and morphologies including slightly corrugated, highly corrugated, or corrugated/hollow depending on the sizes of the original silica microspheres as well as the type of etchant, the etchant concentration and the etching time used.

Figure 4:
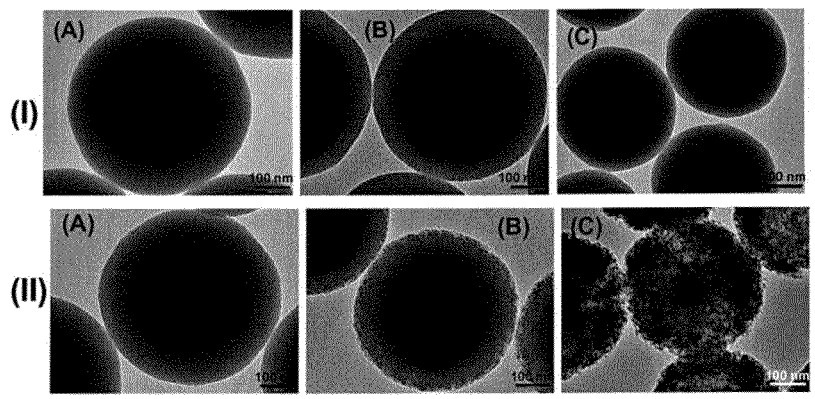
FIGS. 4(I)A-4(I)C and 4(II)A-4(II)C show TEM images of 450 nm diameter silica microspheres, Si450, after etching under stirring with (I) 1 mL of high concentration of KCN solution (0.03 M, pH=11.00) for (A) 1, (B) 4, and (C) 8 h, resulting in samples labeled as Si450-KCN—H1, Si450-KCN—H4, and Si450-KCN—H8, respectively; and (II) 1 mL of high concentration of KOH solution (0.03 M, pH=12.60) for (A) 1, (B) 4, and (C) 8 h, resulting in samples labeled as Si450-KOH—H1, Si450-KOH—H4, and Si450-KOH—H8, respectively, according to an embodiment of the present invention.

As shown in FIG. 4, the TEM images of ~450 nm or large-size silica microspheres, Si450, etched with high concentration of KCN and KOH for 1, 4 and 8 h under shaking are illustrated. The silica microspheres did not exhibit significant change of structure and morphology after etching with a KCN solution, particularly for shorter periods of etching time (FIG. 4). However, as the etching time increased, the etched microspheres showed a slightly corrugated surface (see FIG. 5).

Figure 5:
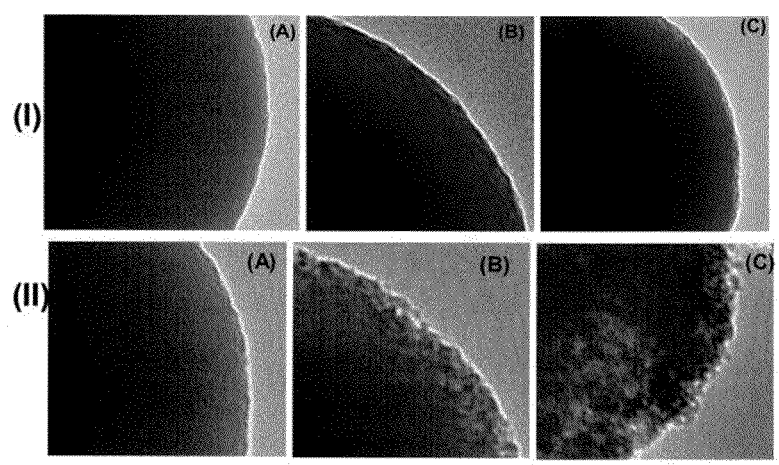
FIGS. 5(I)A-5(I)C and 5(II)A-5(II)C show enlarged TEM images of 100 μL, 10 mg/mL of silica microspheres of average diameter of 450 nm (Si450) after etching with (I) 1 mL of high KCN concentration (0.03 M, ph=11.00) for (A) 1, (B) 4, and (C) 8 h resulting in samples Si450-KCN—H1, Si450-KCN—H4, and Si450-KCN—H8, respectively; and (II) 1 mL of high KOH concentration (0.03 M, pH=12.60 for (A) 1, (B) 4, and (C) 8 h resulting in samples Si450-KOH—H1, Si450-KOH—H4, and Si450-KOH—H8, respectively, according to an embodiment of the present invention.
Figure 6:
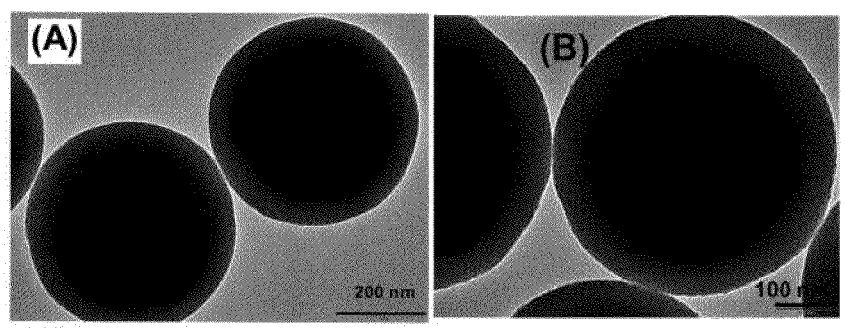
FIGS. 6A-6B show TEM images of 100 μL, 10 mg/mL of silica microspheres of average diameter of 450 nm (Si450) after etching for 4 h with 1 mL of low KOH concentration (pH=10.61), which is of the same pH as the high concentration KCN used, according to an embodiment of the present invention.

The TEM images also revealed that the samples etched with a KOH solution had more pronounced exfoliated and corrugated surfaces than the corresponding samples etched with the same concentration of KCN solution (FIGS. 4 and 5). Furthermore, the samples etched for longer periods in KOH solution exhibited nanoporous and hollow structures while those etched for shorter periods showed only corrugated structures. This indicates that more significant exfoliation of the silica surface took place upon etching the microspheres for longer periods of time (FIGS. 4 and 5). The results also reveal that the treatment of the silica microspheres with KOH solution produces faster and more intense etching compared to the corresponding treatment in KCN solution of a similar concentration. The pH of the KOH solution, in fact, is also higher than that of the same concentration of KCN solution, which is why the former results in a higher degree of etching than the latter. However, it is worth noting that the KCN solution produced a slightly more uniformly etched structure than the KOH solution. Since $K_b$ for the hydrolysis of $CN^-$ ions in aqueous solution is $2.1 \times 10^{-5}$, a 0.03 M solution of KCN is expected to give a theoretical $[OH^-]$ concentration of $\sim 8.0 \times 10^{-4}$ M, which is actually consistent with the measured pH value of ~11.00 or an $[OH^-]$ concentration of $\sim 1.0 \times 10^{-3}$ M. The lower $[OH^-]$ ion concentration in the case of the KCN solution may have resulted in a slower and milder etching of the silica surface compared to the corresponding strongly basic KOH solution, which has an $[OH^-]$ concentration of $\sim 3.0 \times 10^{-2}$ M. On the other hand, the TEM images of the samples Si450-KOH-L4, which were etched for 4 h with a low KOH concentration solution (pH=10.61) (see FIG. 6), did not show as much exfoliation as sample Si450-KOH—H4, which was treated with a high KOH concentration solution for 4 h (FIG. 4). It is worth noting that the former solution has a similar pH as the high KCN concentration (0.03 M). These results proved that the degree of etching of silica and the morphology of the resulting etched microspheres is dependent not only on the type of etchant but also on the concentration of the etchant and the etching time.

Figure 7:
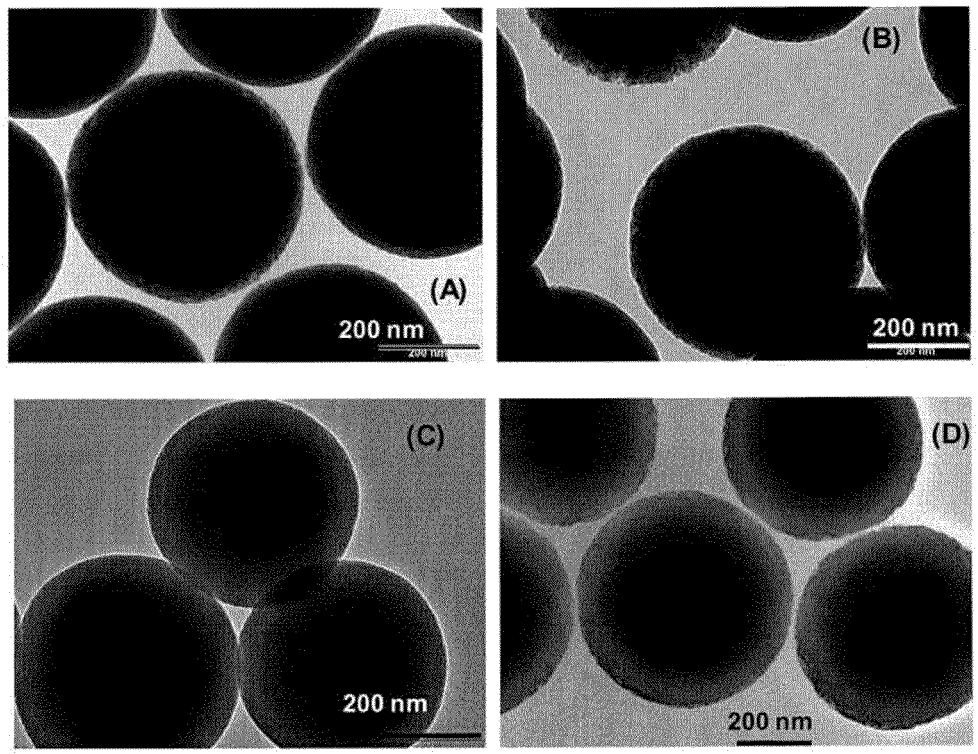
FIGS. 7A-7D show TEM images of 450 nm diameter silica microspheres, Si450, after etching under static condition with 1 mL of high concentration of KCN solution (0.03 M, pH=11.00) for (A) 4, (B) 8, (C) 13 and (D) 23 h, according to an embodiment of the present invention. The images show that the samples contain some particles with significantly exfoliated surface while other particles have barely etched surface.

As shown in FIG. 7, upon etching the silica microspheres, for example Si450, under static condition, the exfoliation of the silica microspheres took place more significantly but non-uniformly. Presumably, the particles in greater contact with the solution and those on the top part of the precipitate underwent more significant etching than those in the bottom part. Interestingly, some of the etched microspheres from the KCN solution under static conditions exhibited more exfoliated surfaces compared to even the corresponding samples etched in a similar solution under shaking as well as compared to the corresponding samples etched with a KOH solution of a similar concentration under shaking (FIG. 7).

EXAMPLE 3

This Example describes the investigation of the effect of the size of the microspheres on the etching described herein.

To investigate the effect of the size of the microspheres, the same mass of smaller sized of silica microspheres, Si250 and Si110, as sample Si450 were taken and subjected to etching under the same conditions.

Figure 8:
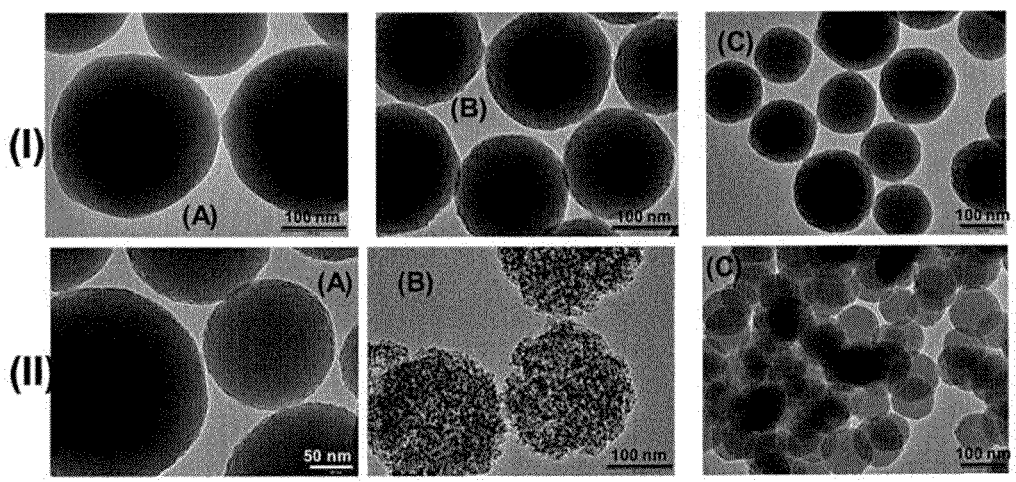
FIGS. 8(I)A-8(I)C and 8(II)A-8(II)C show TEM images of 250 nm diameter silica microspheres, Si250, after etching under stirring with (I) 1 mL of high concentration of KCN (0.03 M, pH=11.00) solution for (A) 1, (B) 4, and (C) 8 h, resulting in samples Si250-KCN—H1, Si250-KCN—H4, and Si250-KCN—H8, respectively; and (II) 1 mL of higher concentration of KOH (0.03 M, pH=12.60) solution for (A) 1, (B) 4, and (C) 8 h, resulting in samples Si250-KOH—H1, Si250-KOH—H4, and Si250-KOH—H8, respectively, according to an embodiment of the present invention.
Figure 9:
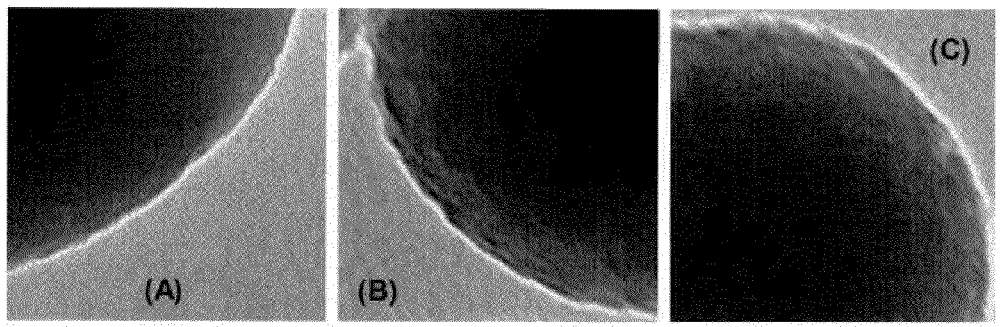
FIGS. 9A-9C show enlarged TEM images of 100 μL, 10 mg/mL of silica microspheres of average diameter of 250 nm (Si250) after etching with 1 mL of low KCN concentration (0.03 M, pH=11.00) for (A) 1, (B) 4, and (C) 8 h resulting in samples Si250-KCN—H1, Si250-KCN—H4, and Si250-KCN—H8, respectively, according to an embodiment of the present invention.
Figure 10:
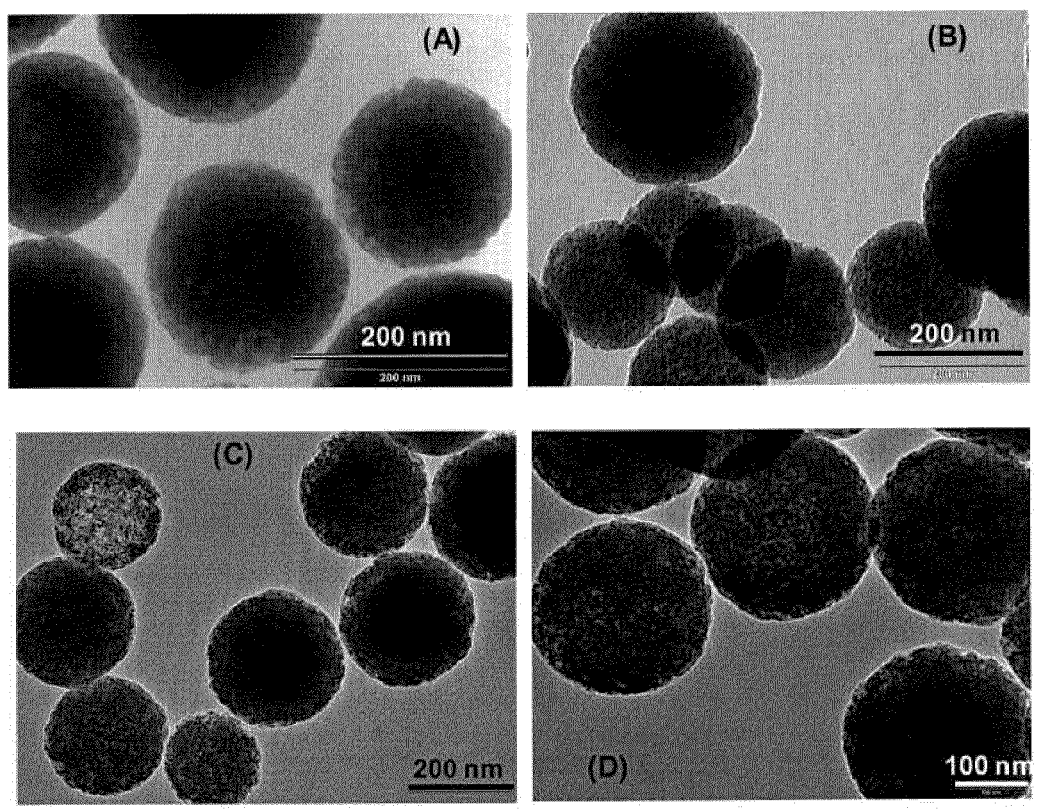
FIGS. 10A-10D show TEM images of 250 nm diameter silica microspheres, Si250, after etching static condition with 1 mL of high concentration of KCN (0.03 M, pH=11.00) solution for (A) 4, (B) 8, (C) 13 and (D) 23 h, according to an embodiment of the present invention.

The results showed that the smaller silica microspheres, Si250, exhibited more pronounced exfoliation and corrugated surface and, in some cases, even hollow structure compared to their bigger counterparts (see FIGS. 8 and 9). The exfoliation of the silica microspheres was more significant again in KOH solution than in KCN solution of the same concentration (FIGS. 8 and 9). This was an interesting observation considering the fact that the total surface area per unit mass or the total number of particles per unit mass was expected to be higher for the smaller microspheres, Si250, than for their bigger counterparts, Si450, and consequently, the relative share of etchant per particle was expected to be less in the former case. Furthermore, the samples Si250 that were etched under static conditions showed some microspheres with more exfoliated surface than the corresponding samples that were etched in a similar solution under shaking. This result is consistent with that obtained for the bigger samples, Si450, above except for slight differences. The differences include the observation of a more significant exfoliation and even complete dissolution of some of the microspheres in the case of the smaller silica microspheres compared to their bigger counterparts, based on the lower amount of product obtained after etching in the former. This was confirmed by a significant change in the size of the microspheres and a reduction in the microsphere's diameter by ~50 nm observed after etching in the smaller size microspheres Si250-KOH—H8 compared to the corresponding etched bigger microspheres, Si450-KOH—H8. Some of the smaller etched microspheres also appeared to have porous structures, especially those etched in KOH solution for 4 and 8 h, i.e. Si250-KOH—H4 and Si250-KOH—H8, respectively. Furthermore, sample Si250 etched under static conditions (FIG. 10) exhibited some microspheres with more significant exfoliated surfaces compared to the corresponding samples etched under stirring (FIGS. 8 and 9). The former also had a more exfoliated surface compared to the corresponding sample Si450 that was etched under static conditions (FIGS. 4 and 7). This result is consistent with what was obtained upon comparing the etched samples Si250 and Si450 under shaking.

Figure 11:
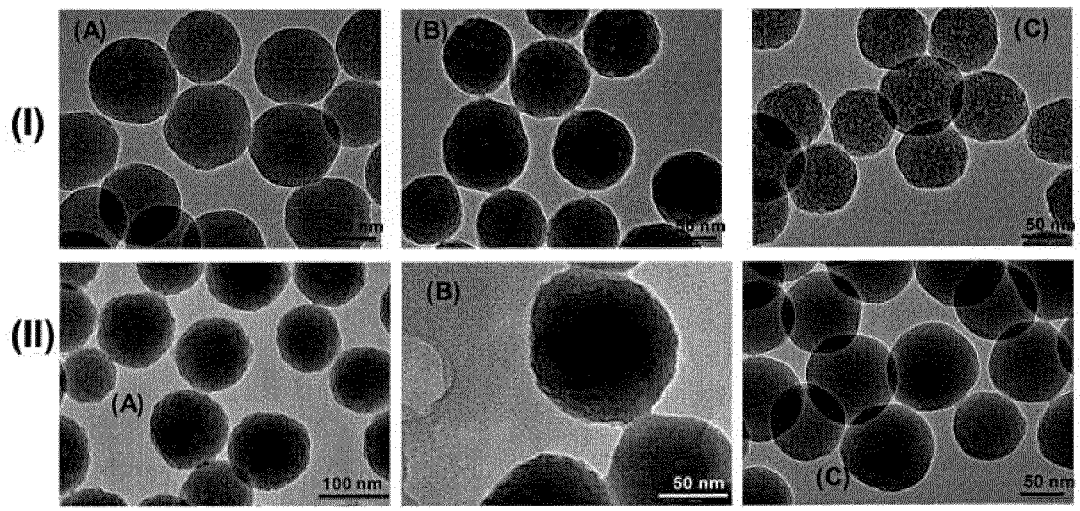
FIGS. 11(I)A-11(I)C and 11(II)A-11(II)C show TEM images of 110 nm diameter silica microspheres, Si110, after etching under stirring with (I) 1 mL of high concentration of KCN (0.03 M, pH=11.00) solution for (A) 1, (B) 4, and (C) 8 h, resulting in samples Si110-KCN—H1, Si110-KCN—H4, and Si110-KCN—H8, respectively; and (II) 1 mL of high concentration of KOH (0.03 M, pH=12.60) solution for (A) 1, (B) 4, and (C) 8 h, resulting in samples Si110-KOH—H1, Si110-KOH—H4, and Si110-KOH—H8, respectively, according to an embodiment of the present invention.
Figure 12:
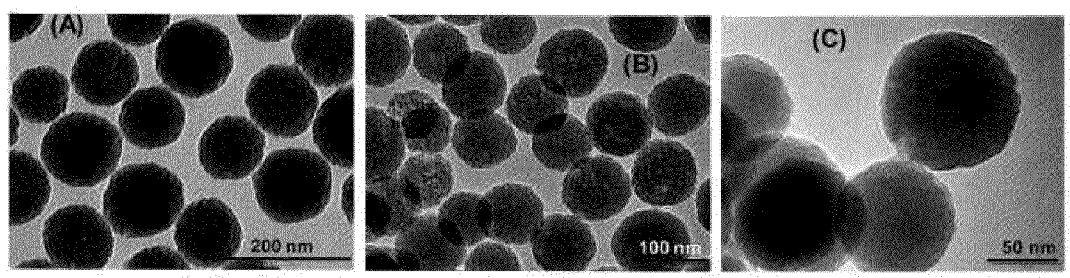
FIGS. 12A-12C show TEM images of 100 μL, 10 mg/mL of silica microspheres of average diameter of 110 nm (Si110)
Figure 13A:
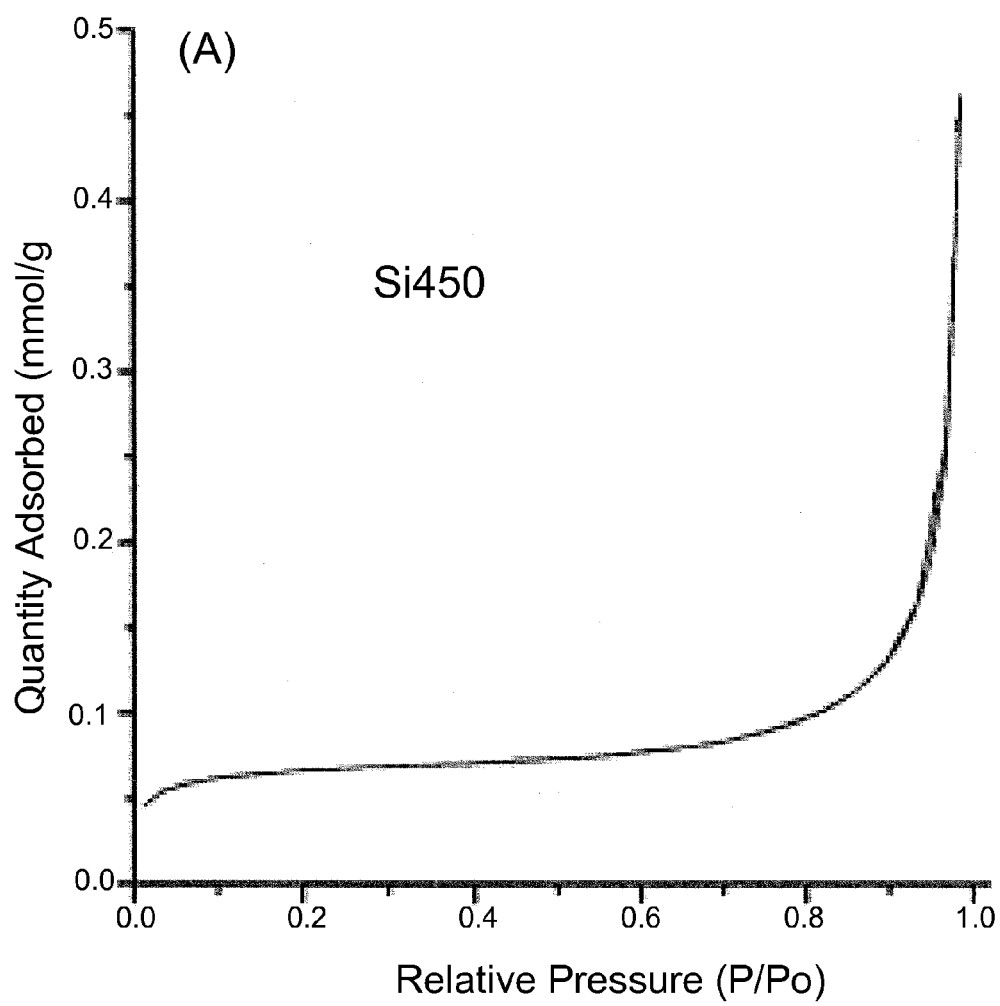
Figure 13B:
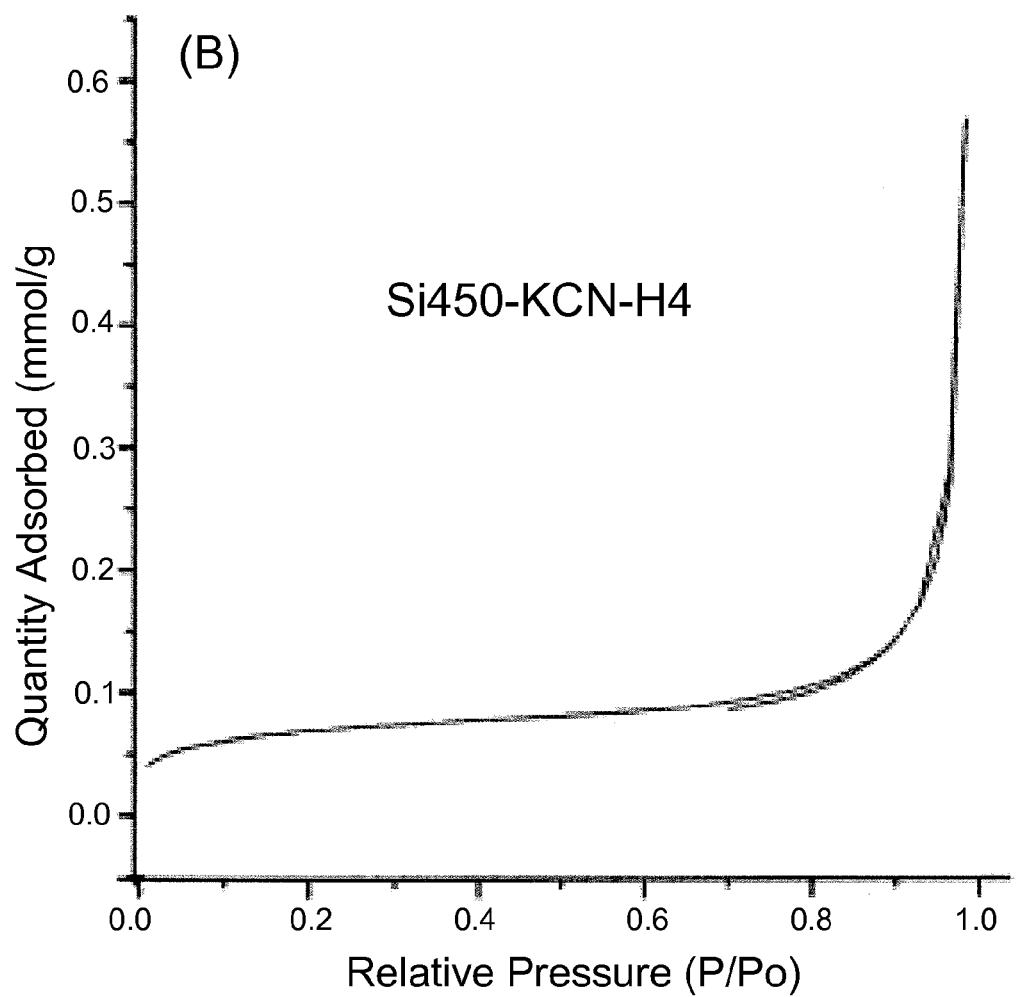
Figure 13C:
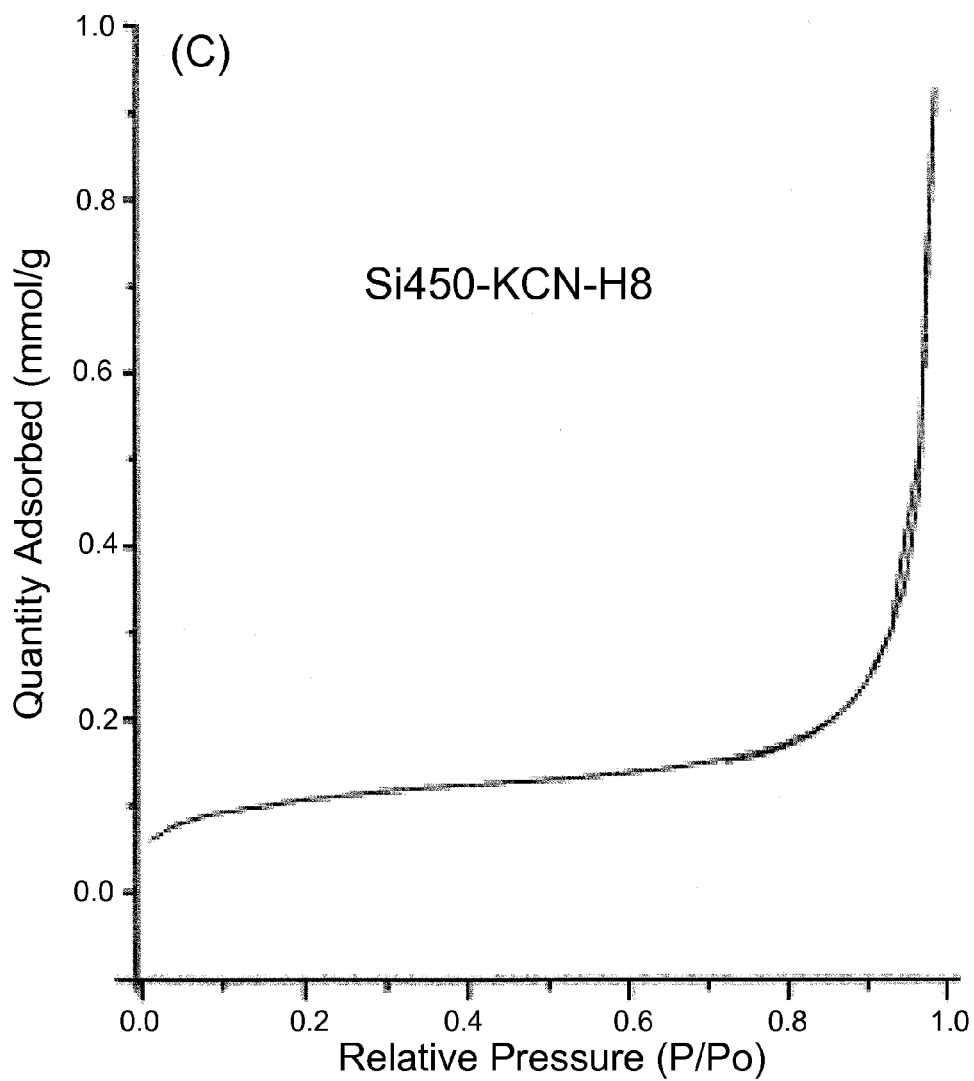
Figure 13D:
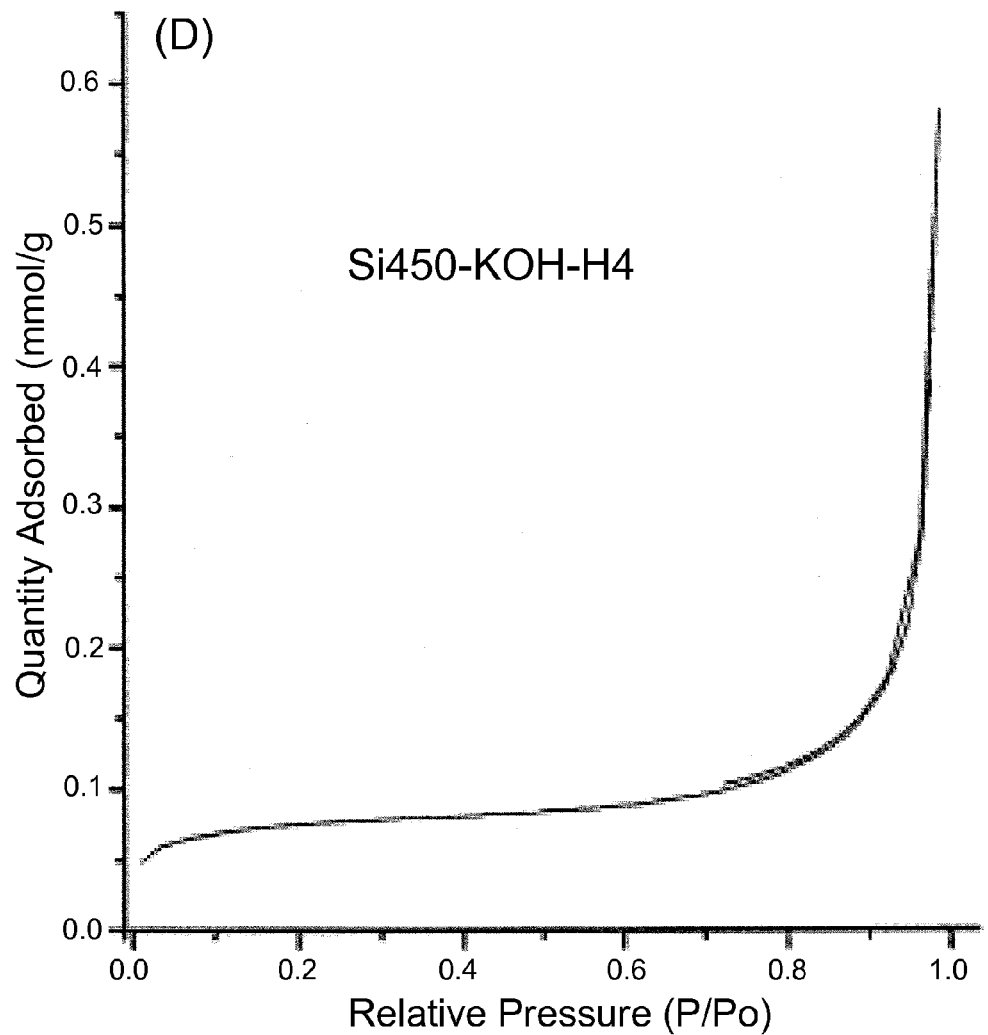
Figure 13E:
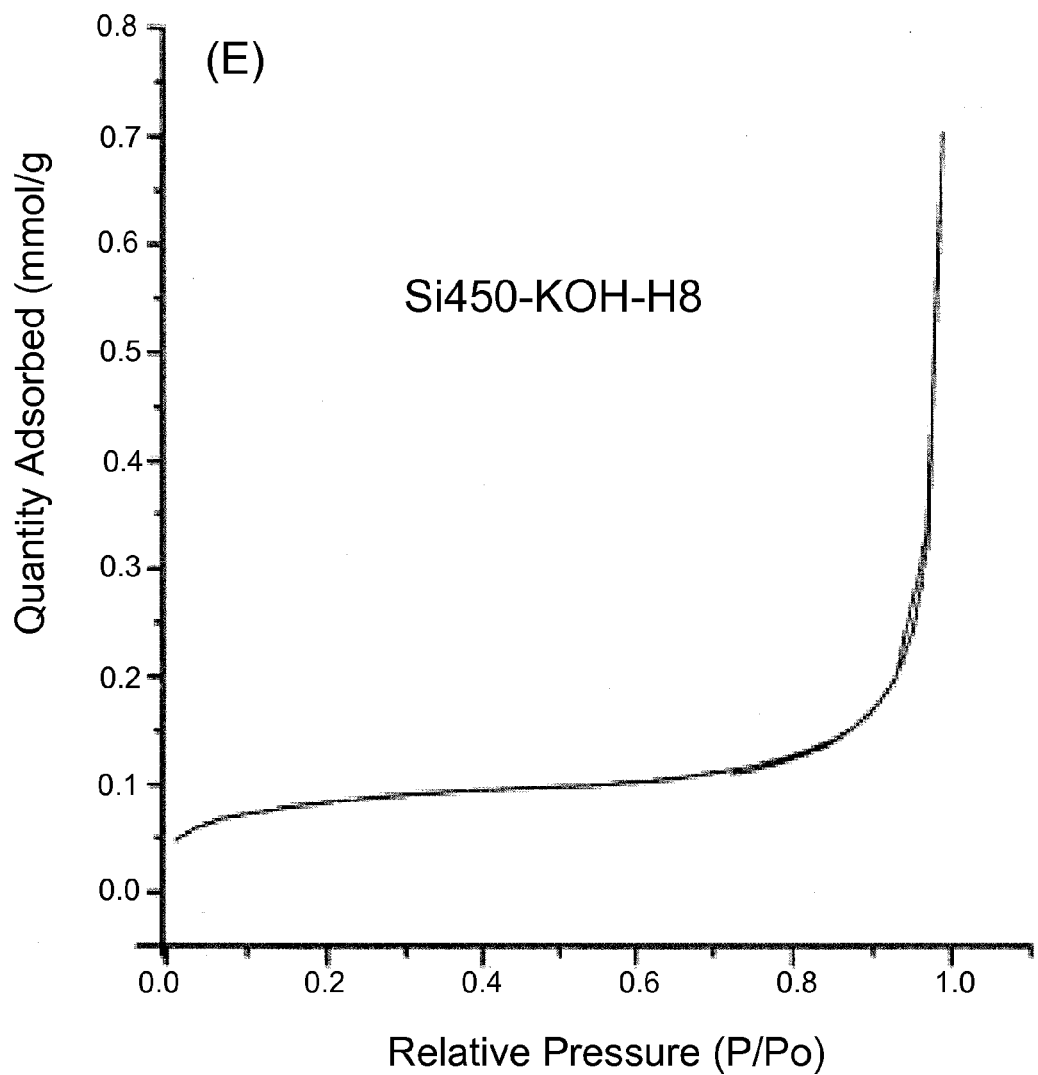

The results also show that the treatment of the smallest size of silica microspheres, Si110, with KOH and KCN solutions has also resulted in etched microspheres, especially after 4 and 8 h of etching time (see FIG. 11). Furthermore, the etchings appeared to be the most significant in this case compared to those in samples Si250 and Si450. Some of the etched Si110 samples also appeared to have hollow and nanoporous structures (FIGS. 11I, C). The etching of sample Si110 under static conditions also showed exfoliation of the silica surface (see FIG. 12) as in samples Si250 and Si450.

EXAMPLE 4

This Example relates to the characterization of the etched silica microspheres by $N_2$ gas adsorption.

The etching of the silica microspheres into different corrugated and hollow structures can obviously be expected to result in an increase in the surface areas of the microspheres. To determine the increase in surface areas in the corrugated and hollow microspheres, the etched silica microspheres were characterized by $N_2$ gas adsorption (see FIG. 13).

The results show that the etched silica microspheres $N_2$ adsorption showed between type I and type II like isotherms, indicating the presence of microporous and macroporous structures in the materials. The adsorption in a higher relative pressure on the isotherms is indicative of the presence of a large degree of macroporosity in the materials, which is created by the exfoliation of the surface of the silica microspheres.

The BJH pore distribution did not show clear differences between the as-prepared and the different etched samples. However, their BET surface areas showed some differences. The BET surface areas of the representative as-prepared and etched microspheres, Si450, Si450-KCN—H4, Si450-KCN—H8, Si450-KOH—H4, and Si450-KOH—H8, were 4.8, 5.3, 6.3, 5.5 and 8.3±0.1 $m^2/g$, respectively, which indicates an increase in surface areas in the order of Si450<Si450-KCN—H4<Si450-KOH—H4<Si450-KCN—H8<Si450-KOH—H8. This result clearly reveals that the surface areas of all the etched microspheres were higher than that of the corresponding as-prepared microspheres. Furthermore, the increase in surface area was higher in microspheres etched with KOH solution than the corresponding microspheres etched with KCN solution of a similar concentration.

The highest surface areas were obtained in the etched samples Si450-KCN—H8, Si450-KOH—H8, and Si450-KOH—H4. This is consistent with the fact these samples, particularly Si450-KOH—H8 and Si450-KOH—H4 microspheres, have more corrugated and hollow structures as observed in their TEM images (FIG. 5II). Also, in the sample Si450-KOH—H8, that was etched with 0.03 M KOH solution for 8 h and in which the highest increase in surface area was observed, the increase in surface area was 73%. This is a significant increase in surface area especially considering the fact that the diameters of the particles are reduced upon etching, albeit only in smaller extent for sample Si450. This surface area increase must have been due partly to the corrugated structure and partly to the hollow structure in sample Si450-KOH—H8. Although there is an increase in surface area in the etched microspheres, their total surface areas are still smaller compared to materials such as mesoporous silica, zeolites, and metal-organic-frameworks (MOFs). However, since the pores and corrugated structures of the etched microspheres are bigger and are mostly on the external surface in the former, they are rather more accessible and well suited to accommodate bigger molecules such as enzymes and nanoparticles compared to the MOFs and zeolites.

EXAMPLE 5

The next several Examples relate to a demonstration of the potential of the corrugated/hollow structures of the etched silica microspheres for chemical (drug) adsorption and for biosensing. This Example relates to the adsorption of rhodamine 6G.

The corrugated/hollow structures on the etched microspheres, produced as discussed supra, were taken advantage of to demonstrate the materials' potential for chemical (drug) adsorption and for biosensing. To demonstrate the etched microspheres' improved potential for chemical (or drug) adsorption, a solution of 1.8 mL of rhodamine 6G (10.4 μM) and 1.5 mg of the as-prepared or etched silica microspheres were mixed with sonication for 30 min. The solutions were then stirred on a shaker for 4 h followed by centrifugation.

The supernatant of the solution was carefully taken and its UV-Vis absorption was measured to determine the concentration of residual rhodamine 6G in it or the mmol of rhodamine 6G adsorbed per mass of sample on the as-prepared and etched microspheres.

The UV-Vis absorption spectra of the supernatant solutions were recorded and the adsorption capacities of the etched and as-prepared materials per unit mass were obtained and compared to one another (see FIG. 14). The results show that the adsorption capacity of the samples increased in the order of Si450<Si450-KCN—H8<Si450-KCN—H4<Si450-KOH—H8<Si450-KOH—H4. This indicates again that the microspheres that were etched with high concentration of KOH solution and which showed more corrugated and porous structure, clearly had higher adsorption capacities for rhodamine 6G. For instance, the adsorption capacity of the etched sample Si450-KOH—H4 was about 1.7 times higher than the corresponding as-prepared sample Si450. The adsorption of rhodamine 6G molecules on silica surface is previously reported to occur via three possible interactions, namely: (1) hydrogen bonding between the surface silanols and the amine groups of R6G molecules; (2) electrostatic interaction; and (3) hydrophobic interaction. Based on this, the improved adsorption capacity by the etched samples for rhodamine 6G (or the differences in the adsorption capacity between the different samples) was attributed to the higher surface areas and the higher density of surface silanol groups in the etched samples. The difference in the surface silanol (—Si—OH) groups was carefully investigated by elemental analysis (Table 1, below). Due to the small quantity of samples obtained in these experiments, Si MAS NMR experiments were not used to quantify the silanol concentrations or in order to compliment the elemental analysis results. Elemental analysis has revealed that the mmol of silanols/g in the samples increased in the order of Si450≅Si450-KCN—H8≅Si450-KOH—H4<Si450-KCN—H4<Si450-KOH—H8. This result indicates that sample Si450-KOH—H8 has the highest silanol concentration per unit mass, in addition to its higher surface area. So, the observed variation in the adsorption capacity of the samples for R6G could be a result of differences in both their surface areas and their mmol of silanols/g sample. Table 1 shows elemental analysis results and percentage of silanols in the parent silica and etched silica microspheres, according to an embodiment of the present invention.

TABLE 1

| Samples | Wt. % C | Wt. % H [a] | Wt. % N [b] | Wt. % H due to Silanols [c] |
|---|---|---|---|---|
| Si450 | <0.10 | 0.94 | 0.42 | 0.86 |
| Si450-KCN-H4 | 0.15 | 0.96 | <0.05 | 0.93 |
| Si450-KCN-H8 | 0.1 | 0.89 | <0.05 | 0.87 |
| Si450-KOH-H4 | 0.17 | 0.88 | <0.05 | 0.84 |
| Si450-KOH-H8 | 0.33 | 1.07 | <0.05 | 1.00 |

[a] Total wt. % H, which is due to residual ethoxy groups, surface silanols and physisorbed ammonia. The presence of possible residual unhydrolyzed ethoxy groups or grafted ethoxy group from ethanol and some physisorbed ammonia was proved by the observed wt. % C and % wt. % N in the samples.
[b] The nitrogen in the samples may be due to some possible physisorbed ammonia and chemisorbed —CN groups. Although the KCN etched samples showed insignificant wt. % N on elemental analysis, their FTIR spectra revealed the presence of strong CN stretching peak (FIG. S6).
[c] The wt. % H due to silanols was obtained by deducting the wt. % H due to ethoxy ($CH_3$—$CH_2$—O) and due to physisorbed $NH_3$ groups from the total wt. % H. That is, [Wt. % H due to silanols] = [Total wt. % H] – [Wt. % H due to ethoxy ($CH_3$—$CH_2$—O) and due to physisorbed $NH_3$ groups].

EXAMPLE 6

This Example relates to the functionalization of the silica microspheres, and to the further confirmation of the effect of surface density of silanols or surface functional groups on the microspheres. Adsorption properties of the samples for R6G after grafting hydrophilic and hydrophobic organosilanes on their surfaces were investigated.

To functionalize the silica microspheres, 100 mg of the as-prepared or etched silica microspheres were dispersed in 5 mL of anhydrous ethanol with sonication. Under vigorous stirring, 200 μL of 3-aminopropyltriethoxysilane (APTMS) or 3-mercaptopropyltriethoxysilane (MPTS) was then added quickly and the solution was stirred for 20 h to graft 3-aminopropyl or 3-mercaptopropyl groups on the surface of the silica microspheres. The functionalized silica microspheres were collected by centrifugation and they then were washed three times with ethanol and let to dry.

The results showed etched microspheres containing hydrophilic organoamine and hydrophobic mercaptopropyl groups (see FIGS. 14B and 14C; and Table 2, below).

TABLE 2

| Silica samples, 450 nm | (Unfunctionalized) [a] | MPTS (—SH Grafted) [a] | APTS ($NH_2$ Grafted) [a] |
|---|---|---|---|
| Si450 | 0.92 | 0.89 | 1.04 |
| Si450-KCN-H4 | 0.70 | 0.56 | 0.82 |
| Si450-KCN-H8 | 0.73 | 0.50 | 0.89 |
| Si450-KOH-H4 | 0.52 | 0.49 | 0.60 |
| Si450-KOH-H8 | 0.66 | 0.48 | 0.83 |

[a] Control experiment of R6G solution (no silica) at the same condition: A = 1.11.

The presence of the functional groups on the etched microspheres was confirmed by elemental analysis. The etched silica microspheres containing hydrophobic 3-mercaptopropyl groups generally exhibited higher adsorption capacity for rhodamine 6G than the corresponding samples functionalized with 3-aminopropyl groups (see Table 2, above). Table 2 shows UV-vis absorbance values of rhodamine 6G (R6G) in the supernatant after stiffing of 1 mL of 10 μM rhodamine 6G solution with 1.5 mg of various functionalized and unfunctionalized, as-prepared and etched silica microspheres for 4 h. [a]The absorption maximum for R6G is, λmax=526.7 nm.

The results showed that this difference between the 3-mercaptopropyl- and the corresponding 3-aminopropyl-functionalized samples were exclusively due to the surface properties or the functional groups as both samples were prepared from the same batch of etched silica microspheres and they, therefore, had similar surface areas. The adsorption capacity for R6G for 3-mercaptopropyl-functionalized microspheres was higher than that of the unfunctionalized microspheres.

The order of increase in adsorption capacity was in the order of Si450<Si450-KCN—H4<Si450-KCN—H8<Si450-KOH—H4<Si450-KOH—H8. This result is consistent with the trend in adsorption capacity as well as the trend in the increase in surface areas that were obtained for the unfunctionalized samples. However, the trend is nearly reversed for the 3-aminopropyl functionalized samples, where the increase in adsorption capacity was in the order of Si450<Si450-KCN—H8<Si450-KOH—H8<Si450-KCN—H4<Si450-KOH—H4. This indicates that samples with higher densities of surface organoamine groups, by virtue of their higher surface areas, have lower adsorption capacity for R6G. The functional groups in various organic-functionalized materials are reported to affect the adsorption properties of different adsorbate molecules in the materials. Furthermore, all the etched silica microspheres, whether they were functionalized or unfunctionalized, showed higher adsorption capacity for R6G than the corresponding unetched samples.

However, the differences in adsorption capacities among the etched samples varied from series to series due to the fact that the surface functional groups on the KCN and KOH etched samples were slightly different. For instance, the samples etched with KCN solution showed a strong peak corresponding to CN stretching (see FIG. 15) despite thorough washing with water and ethanol indicating the presence of trace amounts of chemisorbed CN groups on these samples. The —CN stretching in the FT-IR spectrum of the samples was confirmed by comparing the peak with the spectrum for pure KCN solid sample from Sigma-Aldrich (not shown). However, the elemental analysis of these samples showed very insignificant wt. % N, indicating that there is only trace amount of chemisorbed —CN groups on the KCN etched samples. The surface silanol density in the samples etched with KCN and KOH solutions were also observed to be slightly different.

EXAMPLE 7

This Example relates to the preparation of samples for electrochemical applications. The experiments described in this Example also were designed to take advantage of the resulting materials' increased surface areas and corrugated structures, as discussed in Examples, supra. In brief, the etched corrugated microspheres were used as a platform to effectively anchor gold nanoparticles and horseradish peroxidase (HRP) via the gold nanoparticles (see FIG. 16, discussed further below) and in order to fabricate a biosensor for quantitative determination of $H_2O_2$ (see FIG. 17, discussed further below). The preparation of electrochemical biosensors and determination of micromolae $H_2O_2$ concentration is discussed below.

Electrochemical biosensors on a glassy carbon electrode were assembled by using the as-prepared and etched silica microspheres as the platform. First, 100 μL of 3-aminopropyltrimethoxysilane (APTS) was added quickly under vigorous stirring into a solution containing 0.05 g of dry as-prepared or etched silica microspheres and 5 mL of ethanol in order to functionalize the surface of the silica with amine groups. After 12 h stiffing, the solution was centrifuged and the supernatant was decanted. The excess APTS on the precipitate was washed off with ethanol by centrifugation and decantation. The precipitate was let to dry under ambient conditions.

Then, 2.6 mg of the dry amine-functionalized silica microspheres sample was sonicated in 5 mL solution containing gold nanoparticles (AuNP), which were synthesized by the Turkevich method. In a typical Turkevich synthesis, 0.6 mL of $NaBH_4$ (10 mM, in 0.025 M sodium citrate solution) was quickly added under vigorous stirring into 19.8 mL of $HAuCl_4$ (250 μM) and 0.2 mL of sodium citrate (0.025 M) and then solution was stirred for 40 s.

The gold anchored amine-functionalized silica microspheres were collected by centrifugation. The supernatant in all cases remained red, revealing that the concentration of the gold nanoparticles in the solution was large enough to saturate the surface of the silica microspheres. The precipitate was washed with deionized water (5 mL) three times and then dispersed in 1 mL of horseradish peroxidase (HRP) (1 mg/mL, in PBS buffer) solution. The mixture was then stirred on a shaker for 1 h. After centrifugation and washing the precipitate carefully with Millipore water three times, a red precipitate of Silica-AuNP-HRP (or $SiO_2$—AuNP-HRP) composite nano-bioconjugate microspheres was obtained. The resulting $SiO_2$—AuNP-HRP microspheres were dispersed in 100 μL Millipore water and stored in a fridge at 4° C. until use.

A glassy carbon electrode (GCE) was polished successively with 3.0 and 1.0 μm of diamond suspensions, and 0.05 μm of alumina suspension for 5 min. The electrode was then rinsed thoroughly with methanol, sonicated in doubly distilled water, and allowed to dry at room temperature. Then, 5 μL of the $SiO_2$—AuNP-HRP microspheres obtained above was deposited on the surface of the pretreated GCE and left to dry at room temperature. A silica sol (10 μL) was prepared as reported previously by mixing 600 μL of ethanol, 50 μL of TEOS, 10 μL of 5 mM NaOH, and 60 μL of water in a small test tube at room temperature and then by sonicating the solution for 30 min. The sol was kept in a fridge at 4° C. when not in use. This silica sol was then poured over the $SiO_2$—AuNP-HRP that was present on the GCE in order to encapsulate the $SiO_2$—AuNP-HRP with a thin layer of silica. The electrode was then stored at 4° C. for 12 h prior to use as a biosensor for the determination of micromolar $H_2O_2$ concentration.

The electrochemical measurements were carried out in a phosphate buffer solution (pH=7.2), which was purged with high-purity nitrogen prior to each experiment. A conventional three-electrode system containing the silica modified electrode as the working electrode, a platinum wire as the auxiliary electrode, and a KCl (3 M) electrode as the reference electrode were used. All the step curves were collected at the potential of −0.35 V relative to the reference electrode.

Figure 16:
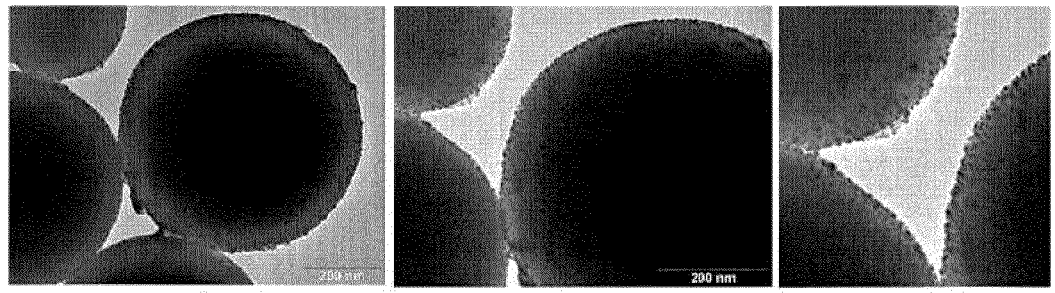
Figure 16:
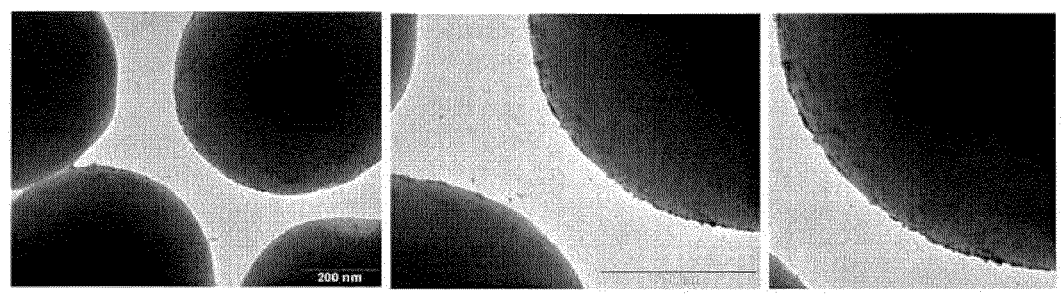
Figure 16:
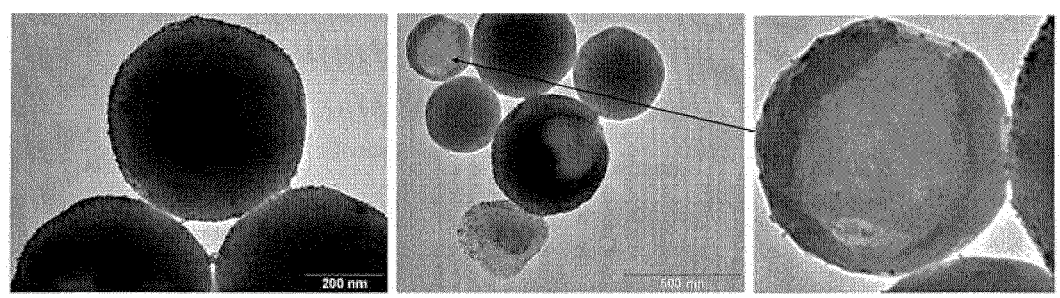

The TEM image results in FIG. 16 show Au nanoparticles anchored onto the corrugated surfaces and in the hollow structures of the etched silica microspheres. A typical cyclic voltammetry graph of the as-prepared and the etched silica microspheres conjugated with Au nanoparticles and HRP in PBS (pH=7.2) is shown in FIG. 17A. The graph exhibits a pair of redox peaks located at about −0.3 and −0.1 V corresponding to the embedded HRP. This redox peak is observed only in the samples containing HRP and it is not observed in the control sample containing no HRP (FIG. 17A, a). The electrocatalytic reduction of $H_2O_2$ on the GC electrodes modified by the Au—HRP—$SiO_2$ microspheres was also tested by amperometry, which is one of the most common used techniques in electrochemical biosensors. FIG. 17B illustrates that when 50 μL of 250 mM $H_2O_2$ was added to the PBS electrolyte, the current response of the sensors was rapidly enhanced and approached about 98% of its steady state current within 5 s. This may be ascribed to the increase in conductivity of the $SiO_2$—AuNP-HRP microspheres matrix by the presence of Au NPs.

The trend in the electrochemical response to the same concentration and volume of $H_2O_2$ by the same mass of microspheres on the electrode was Si450-KCN—H4≅Si450-KCN—H8<Si450≅Si450-KOH—H8<Si450-KOH—H4. Interestingly, the electrocatalytic current or electrocatalytic response of the biosensor fabricated from the KOH-etched silica microspheres was higher than those prepared from the corresponding unetched microspheres; and the electrocatalytic current in the latter in turn was greater than those prepared from the corresponding KCN-etched silica microspheres.

Furthermore, the biosensor with the silica microspheres etched with a high concentration of KOH for 4 h, Si450-KOH—H4, showed the highest current response under the same experimental conditions and it resulted in the most sensitive $H_2O_2$ biosensor among the series of samples that were investigated. Based on the TEM images (FIG. 4) and the BET surface area data, the largest electrochemical response obtained from a biosensor fabricated from Si450-KOH—H4 is not surprising. This sample has among the highest surface area per unit mass as well as it appeared to have accessible pore structures on its external surface that seem to be capable of accommodating Au nanoparticles of ~15 nm diameter and HRP molecules of ~2.5-3 nm in size as judged from its TEM image (see FIGS. 4 and 5).

Although, sample Si450-KOH—H8 has, in fact, a higher surface area than sample Si450-KOH—H4, most of the pore structures in the former do not appear to be on the accessible external surface but instead in small micropores underneath, as judged from its TEM images. Consequently, the pores in the former do not seem to be capable of accommodating the Au nanoparticles and the HRP molecules as much, resulting in a lower electrochemical response. This was further confirmed by the significantly less intense reduction peak of gold nanoparticles at ~0.2 V versus Ag/AgCl (3.0 M) in the cyclic voltammetry (CV) curves of Si450-KOH—H8 compared to that for Si450-KOH—H4 and Si450-KCN—H4. The slight shift of this reduction peak to a negative potential compared to gold nanoparticles on a naked electrode is most likely because of the difficulty for the electron transfer reaction between the gold nanoparticles and the electrode by the insulation of the nanoparticles with the silica layer deposited over the $SiO_2$—AuNP—HRP microspheres.

Although sample Si450-KCN—H4, which was etched with KCN solution, showed a higher reduction peak than sample Si450-KOH—H4, its current response or biosensing activity was much lower, even lower than the as-prepared silica microspheres. This might be ascribed to the presence of the trace amount of cyanide ions on this sample as proven by FT-IR spectrum (FIG. 15). It was proposed that horseradish peroxidase is reversibly inhibited by ions such as cyanide and sulfide at a concentration of $10^{-5}$ M.

The controlled etching synthetic method to corrugated and hollow microspheres, as discussed in the Examples herein for silica microspheres, was also proved to be applicable to other metal oxide microspheres (see discussion in the Example, infra).

EXAMPLE 8

This Example relates to the synthesis and etching of titania microspheres, in place of the silica microspheres as discussed supra. The synthesis of the titania microspheres is discussed below.

In brief, monodisperse spherical titania microspheres were prepared by controlled hydrolysis of titanium tetraalkoxide in ethanol. Typically, 1.8 mL of titanium butoxide was added to a solution containing 100 mL ethanol and 0.5 mL of KCl (0.12 M). The solution was then kept at ambient condition under stirring for 10 min and subsequently under static condition for 5 h. The resulting white precipitate was collected by centrifugation and washed with ethanol prior to drying in air.

Figure 18:
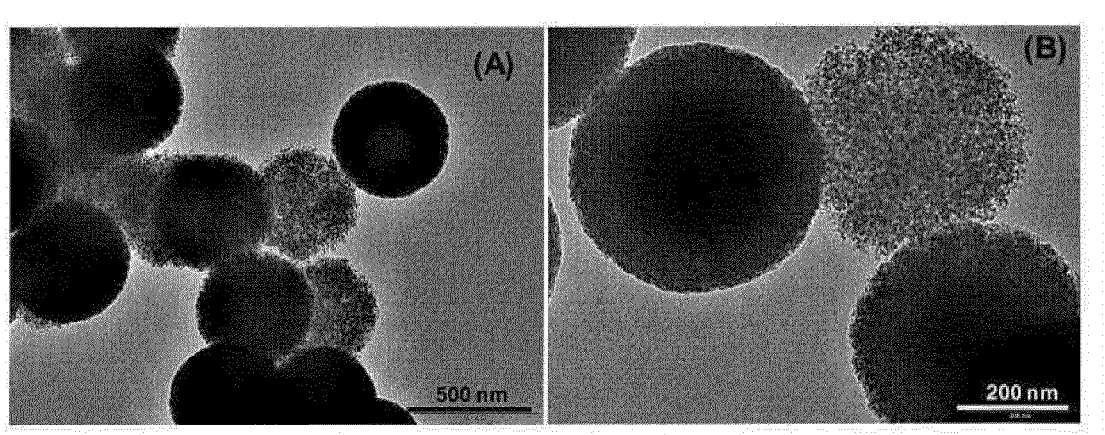

By using the same procedure as discussed with respect to the etching of silica microspheres in the previous Examples, it was demonstrated that the etching of titania ($TiO_2$) microspheres of ~400 nm in diameter into highly nanoporous and corrugated $TiO_2$ microspheres (see FIG. 18). However, the etching of the $TiO_2$ microspheres for 4 h compared to etching for 8 h did not show significant differences as in silica microspheres. This result illustrated the versatility of the synthetic method.

The previous Examples described the synthesis of new classes of corrugated and hollow silica microspheres (~100-450 nm) by controlled etching of smooth, spherical Stöber silica microspheres with aqueous KCN or KOH solutions. By varying the type and the concentration of the etchant and the etching time, the morphology and the structure of silica microspheres, as well as the increase their surface areas, were able to be controlled.

The resulting etched microspheres containing corrugated and nanoporous structures were proven to have unique surface properties such as improved surface areas and adsorption capacity for different chemical reagents. In addition, by encapsulating gold nanoparticles and electroactive species such as horseradish peroxidase via the gold nanoparticles onto the corrugated and hollow etched silica microspheres, enhanced electron transport properties and highly sensitive biosensors for the detection of micromolar concentrations of $H_2O_2$ was demonstrated.

This new controlled etching synthetic method to prepare unique corrugated and microporous microspheres (e.g., silica or other metal oxide microspheres such as $TiO_2$) is simple and versatile. The latter has been demonstrated by etching $TiO_2$ microspheres into corrugated and nanoporous titania microspheres. The unique structures created by this new synthetic approach results in nanomaterials with better surface properties and morphology for various applications. These etched microspheres may also produce unique photonic crystals, in which infiltration and mass transport of solutions and precursors in the void spaces of their colloidal crystals would be easier due to the corrugated and porous structures of the microspheres. Consequently, the formation of well-ordered opal and inverse opal materials, without defect structures, can become easier to achieve.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the disclosed invention.

What is claimed is:

1. A method of synthesizing corrugated and nanoporous silica microspheres comprising the steps of:
   a. synthesizing a plurality of silica microspheres consisting of silica; and
   b. wet-etching the surface of each of said plurality of said silica microspheres with an etchant comprising a basic solution having a pH above 10.00, wherein said basic solution comprises a solution selected from the group consisting of an aqueous potassium cyanide solution and an aqueous potassium hydroxide solution, and wherein said step of wet-etching comprises contacting the surface of each of said plurality of said silica microspheres with said etchant under conditions sufficient to produce silica microspheres having corrugated and nanoporous surfaces.

2. The method of claim 1, wherein the step of synthesizing further comprises synthesizing the plurality of silica microspheres to have diameters of between 50 nm and 600 nm.

3. The method of claim 1, wherein said basic solution comprises a solution having a pH between 10.00 and 13.00.

4. The method of claim 3, wherein the step of wet-etching further comprises etching said silica microspheres under a non-static mixing condition for 1 to 8 hours.

5. The method of claim 4, wherein said non-static mixing condition comprises the step of shaking or stirring said silica microspheres.

6. The method of claim 5, further comprising the step of adsorbing a chemical or drug onto said synthesized corrugated and nanoporous microspheres, thereby obtaining a chemical- or drug-adsorbed corrugated and nanoporous silica microspheres.

7. The method of claim 6, wherein said chemical is Rhodamine 6G.

8. The method of claim 5, further comprising the step of functionalizing the surface of at least one of said synthesized corrugated and nanoporous microspheres, comprising grafting at least one of a hydrophilic organosilane and a hydrophobic organosilane onto the surface of at least one of said synthesized corrugated and nanoporous microspheres.

9. The method of claim 8, wherein said hydrophilic organosilane comprises 3-aminopropyltriethoxysilane.

10. The method of claim 8, wherein said hydrophobic organosilane comprises 3-mercaptopropyltriethoxysilane.

11. The method of claim 8, further comprising the step of adsorbing a chemical or drug onto said functionalized corrugated and nanoporous microspheres, thereby obtaining a chemical- or drug-adsorbed corrugated and nanoporous silica microspheres.

12. The method of claim 11, wherein said chemical is Rhodamine 6G.

13. The method of claim 5, further comprising the step of functionalizing the surface of at least one of said synthesized corrugated and nanoporous microspheres with amine groups.

14. The method of claim 13, further comprising the step of anchoring gold nanoparticles onto at least one of said amine-functionalized corrugated and nanoporous microspheres.

15. The method of claim 14, further comprising the step of anchoring horseradish peroxidase (HRP) onto the gold nanoparticles that are anchored onto at least one of said amine-functionalized corrugated and nanoporous silica microspheres, thereby obtaining at least one silica microsphere-anchored horseradish peroxidase.

16. A method of making an electrode having immobilized thereupon a layer of horseradish peroxidase, the method comprising: coating a glassy carbon electrode with the particles of claim 15.

17. A method of detecting hydrogen peroxide ($H_2O_2$) in a sample, comprising the steps of:
  a. providing an electrode produced according to the method of claim 16,
  b. encapsulating the electrode by applying a silica sol thereto, said sol obtained by sonicating a solution of silica, thereby producing an $H_2O_2$-biosensing electrode;
  c. contacting the $H_2O_2$-biosensing electrode with a solution suspected of containing $H_2O_2$, wherein the biosensing electrode is capable of detecting micromolar concentrations of $H_2O_2$; and
  d. voltammetrically determining the sample $H_2O_2$ concentration.

* * * * *